United States Patent [19]

Hayano

[11] Patent Number: 5,663,569

[45] Date of Patent: Sep. 2, 1997

[54] DEFECT INSPECTION METHOD AND APPARATUS, AND DEFECT DISPLAY METHOD

[75] Inventor: Fuminori Hayano, Tokyo, Japan

[73] Assignee: Nikon Corporation, Tokyo, Japan

[21] Appl. No.: 318,551

[22] Filed: Oct. 5, 1994

[30] Foreign Application Priority Data

Oct. 14, 1993 [JP] Japan .................................. 5-256602
Oct. 21, 1993 [JP] Japan .................................. 5-263366

[51] Int. Cl.$^6$ .................................................. G01N 21/86
[52] U.S. Cl. .......................... 250/559.45; 250/559.06; 356/431; 382/149
[58] Field of Search ........................ 250/559.49, 559.48, 250/559.45, 559.04, 559.06, 559.22, 559.2; 356/237, 394, 398, 430, 431; 382/149, 145, 148; 345/116

[56] References Cited

U.S. PATENT DOCUMENTS 4,978,224 12/1990 Kishimoto et al. ..................... 356/394
4,982,105 1/1991 Takahashi ............................ 250/559.06

*Primary Examiner*—Que Le
*Attorney, Agent, or Firm*—Shapiro and Shapiro

[57] ABSTRACT

In a defect inspection method, inspection light is irradiated onto the surface to be inspected of an object to be inspected, a defect on the surface to be inspected is detected on the basis of a signal obtained by photoelectrically converting scattered light of the inspection light from the surface to be inspected, and the size of the detected defect is determined. When a plurality of defects are detected, the detected defects are observed at a predetermined magnification in the order from larger defects on the basis of the determination result. When a defective portion is found as a result of the observation, defect inspection of the object to be inspected is terminated.

16 Claims, 12 Drawing Sheets

| ADDRESS | DATA |
|---|---|
| 1 | $(X_1, Y_1, V_1)$ |
| 2 | $(X_2, Y_2, V_2)$ |
| 3 | $(X_3, Y_3, V_3)$ |
| 4 | $(X_4, Y_4, V_4)$ |

| ADDRESS | DATA |
|---|---|
| 1 | $(X_4, Y_4, V_4)$ |
| 2 | $(X_7, Y_7, V_7)$ |
| 3 | $(X_2, Y_2, V_2)$ |
| 4 | $(X_9, Y_9, V_9)$ |

DEFECT INSPECTION METHOD AND APPARATUS, AND DEFECT DISPLAY METHOD

BACKGROUND OF THE INVENTION

1. Field of the Invention

The present invention relates to a defect inspection method and apparatus, which are suitably applied to inspections of defects such as foreign matters, which become attached to the surface of a mask or reticle (to be collectively referred to as a "reticle" hereinafter) used in the exposure process in the manufacture of, e.g., semiconductor elements or the surface of a pellicle (anti-dust film), which is formed to be separated by a predetermined interval from the surface of the reticle.

2. Related Background Art

When defects such as foreign matters are present on the surface of a reticle for exposure used in the manufacture of, e.g., semiconductor elements, using a photolithography technique, the manufacturing yield of the semiconductor elements is lowered. In order to avoid this, the states of defects on the reticle surface are conventionally inspected, before exposure, using a defect inspection apparatus. In order to prevent foreign matters from becoming directly attached to the pattern formation surface of the reticle and its rear surface, an anti-dust film called a pellicle is often extended on the surface of the reticle. Since such a pellicle is in a defocus state from the pattern formation surface of the reticle conjugate with the exposure surface of a photosensitive substrate (e.g., a wafer), if foreign matters have the same size, their influence if attached to the pellicle is smaller than if directly attached to the reticle.

However, when the size of foreign matters exceeds a predetermined limit, even foreign matters attached to the pellicle influence the exposure result. As for the front surfaces and rear surfaces (the surfaces on the side of the reticle) of the pellicle, the states of defects such as foreign matters are inspected by the defect inspection apparatus. In the following description, a reticle is used as an object to be subjected to defect inspection, and the reticle is assumed to include one on which a pellicle is formed.

FIG. 7 shows an example of a conventional defect inspection apparatus. Referring to FIG. 7, a reticle 1 is placed on a stage 2, and the stage 2 is movable in the Y direction by a driving unit 3. The moving amount, in the Y direction, of the stage 2 is always measured by a distance measurement device 4 such as a linear encoder, and a position signal S1 indicating the distance measurement value of the distance measurement device 4 is supplied to a signal processing circuit 5. In addition, a light beam L1 emitted from a light source (not shown; e.g., 8 laser light source) is reflected and deflected by a galvano scanner 6 (or, e.g., a polygonal scanner), which is vibrated by a driving unit 7. The deflected beam L1 is converted into a light beam L2, which converges on the reticle 1, via a scanning lens 8, and scans, in the X direction, a scanning line 10 substantially parallel to the X direction on the reticle 1. When the light beam L2 is scanned in the X direction, and the reticle 1 is moved in the Y direction by the driving unit 3 at a speed lower than the scanning speed, the entire surface of the reticle 1 can be scanned with the light beam.

If a defect such as a foreign matter 11 is present on the surface of the reticle 1, scattered light L3 of the light beam L2 from the foreign matter 11 is generated. The scattered light L3 is focused on the light-receiving surface of a photoelectric detector 13 such as a photomultiplier via a light-receiving lens 12, and a detection signal S3 obtained by photoelectrically converting the focused light in the photoelectric detector 13 is supplied to the signal processing circuit 5. The signal processing circuit 5 also receives a deflection angle signal S2 supplied to the driving unit 7 for the galvano scanner 6, and can determine the presence of the foreign matter 11 on the basis of the detection signal S3. Parallel to this processing, the signal processing circuit 5 can recognize the position of the foreign matter 11 on the basis of the position signal S1 from the distance measurement device 4 and the deflection angle signal S2 for the driving unit 7 from the galvano scanner 6 obtained when a signal indicating the foreign matter 11 appears in the detection signal S3. More specifically, the X-coordinate of the foreign matter 11 can be detected from the deflection angle signal S2, and the Y-coordinate of the foreign matter 11 can be detected from the position signal S1.

Since the amount of the scattered light L3 becomes larger as the size of the foreign matter becomes larger, the magnitude of the detection signal S3 from the photoelectric detector 13 indicates the size of the foreign matter. For this reason, the signal processing circuit 5 can display the attached position (X, Y) and size of the foreign matter on a CRT display 14 in the form of, e.g., a table. Alternatively, the signal processing circuit 5 can display the coordinates (X, Y) and size of the foreign matter, which are detected simultaneously with scanning of the light beam on the reticle 1, on the display screen of the CRT display 14 in the form of a two-dimensional map. Furthermore, after the position (X, Y) and size (the value of the detection signal S3) of the detected foreign matter are stored in a storage unit such as a memory in the signal processing circuit 5, the stored position and size can be read out from the storage unit after the end of inspection, and can be displayed on the CRT display 14 in the form of a two-dimensional map or a table, or can be printed out by a printer (not shown).

FIG. 8 shows a display example of a map on the CRT display 14. In this display example, the surface of the reticle 1 shown in FIG. 7 is divided into a large number of small rectangular regions (to be referred to as "cells" hereinafter), and foreign matter information on the entire surface of the reticle 1 is displayed in a rectangular window 17 on the display screen in FIG. 7 in units of cells. More specifically, as shown in FIG. 7, the surface of the reticle 1 is partitioned at predetermined pitches in both the X and Y directions to be divided into a large number of small (1- or 5-mm square) cells C(1, 1), C(1, 2), C(1, 3), . . . , C(2, 1), . . . The window 17 on the display screen in FIG. 8 is divided into display cells P(1, 1), P(1, 2), P(1, 3), . . . , P(2, 1), . . . in one-to-one correspondence with the cells on the reticle 1 in FIG. 7, and symbols A, B, and C indicating defects such as foreign matters are displayed in units of display cells.

In this case, the X and Y directions in FIG. 7 respectively correspond to X1 and Y1 directions in FIG. 8, and defects are displayed on display cells P(i, j) corresponding to cells C(i, j) to which coordinates (X, Y), where defects are detected, respectively belong, while being classified into ranks such as symbols A, B, and C in correspondence with the signal strengths of the detection signal S3. The symbols A, B, and C are ranks representing the sizes of defects. For example, when the detection signal S3 is small, a rank "A" representing a small defect is displayed; when the detection signal S3 is large, a rank "C" representing a large defect is displayed.

It should be noted that the following considerations apply to the defect inspection process.

(i) When detection signals S3 indicating foreign matters are obtained at two different coordinate positions within a single cell, the signal intensity of the larger detection signal. S3 and the coordinate position at that time are adopted as defect data in that cell. Normally, a larger defect poses a problem. For example, when a detection signal with a value "50" and a detection signal with a value "100" are obtained at different positions in a 1-mm square cell, the signal with the value "100" and the coordinate position where this detection signal is obtained are used as defect data of the cell.

(ii) Since the detection signal S3 includes electrical signal components and noise components due to very weak light other than scattered light from the foreign matter, a detection signal S3 having a value equal to or larger than a predetermined threshold value is used as defect data.

Another example of the conventional defect inspection apparatus will be described below with reference to FIG. 9. Referring to FIG. 9, a reticle 1 is placed on a stage 2, and the stage 2 is moved in the Y direction by a driving unit 3. The moving amount, in the Y direction, of the stage 2 is measured by a distance measurement device 4. A light beam L4 emitted from a light source 16 such as a laser light source is converted into a substantially collimated slit beam L5 by a lens system 19 comprising a cylindrical lens 18 and a collimator lens 18, and the slit beam L5 is obliquely irradiated onto the reticle 1. For this reason, on the reticle 1, a slit-shaped irradiation region 20 parallel to the X direction is irradiated by the slit beam L5.

Of course, when a defect such as a foreign matter 21 is present in the slit-shaped irradiation region 20, scattered light L6 is generated from the defect, and forms a defect image on a one-dimensional image pickup element 23 such as a one-dimensional CCD. In this case, the slit-shaped irradiation region 20 and the image pickup surface of the one-dimensional image pickup element 23 have a substantially optically conjugate positional relationship via a light-receiving lens 22. Therefore, in the apparatus shown in FIG. 9, the Y-coordinate of the attached position of the foreign matter 21 is measured by the distance measurement device 4, and the X-coordinate of the attached position is identified based on the pixel number of the one-dimensional image pickup element 23 on which the optical image of the foreign matter is formed. Furthermore, the sizes of foreign matters can be classified into ranks in correspondence with the strength of a detection signal S4 as a photoelectric conversion signal (image pickup signal) obtained from each pixel of the one-dimensional image pickup element 23. For this reason, the same map as in the apparatus shown in FIG. 7 can be displayed on a display device such as a CRT display.

More specifically, in the apparatus shown in FIG. 9 as well, the surface of the reticle 1 is divided into a large number of cells C(1, 1), C(1, 2), . . . , and a window 17 in FIG. 10 corresponding to the entire surface of the reticle 1 on the screen of the display device is divided into display cells P(1, 1), P(1, 2), . . . in correspondence with cells on the reticle 1. The states of defects are displayed on the display cells while being classified into ranks A, B, and C.

In in the above-mentioned prior art, when a large foreign matter is present on the reticle 1, defects are successively displayed as if two foreign matters were present adjacent to each other like on display cells P(2, 5) and P(2, 6) and display cells P(5, 6) and P(5, 7) in the window 15 as the display map, as shown in FIG. 10. Such a display error tends to occur when the size of the cell C(i, j) on the reticle 1 is small. More specifically, display errors occur more easily in the case of 1-mm square cells than in 5-mm square cells.

The defect inspection apparatus is often provided with an observation unit 15 shown in FIG. 7 to allow observation of defects. Referring to FIG. 7, the observation unit 15 is attached to a slider 16 to be slidable in the X direction. As the observation method of the observation unit 15 itself, a visual observation mode for observing defect portions on the surface of the reticle 1 using an optical microscope is available, or as another observation method, an image observation mode for picking up an optical image obtained by the observation unit 15 using a two-dimensional image pickup element (e.g., a CCD), and displaying the picked-up image on a TV monitor is available. In general, even when a foreign matter having a predetermined size becomes attached onto the surface of the reticle 1, if the attached position corresponds to a light-shielding portion coated with, e.g., a chromium film, the influence on the exposure result is small. However, if the attached position corresponds to a light-transmitting portion, the influence on the exposure result is large. More specifically, even when foreign matters having the same size become attached to the surface of the reticle 1, the use of the reticle 1 is enabled or impaired depending on the attached positions of the foreign matters. For this reason, by observing defects detected upon light beam scanning using the observation unit 15, whether or not the reticle 1 can be used is finally determined.

When the observation unit is arranged in this manner, a 1- or 5-mm square cell size, and in some cases, a 0.1-mm square cell size are used as the size of the cells C(i, j) on the reticle 1 in correspondence with the size of the observation field of the observation unit (when various observation magnifications such as low, medium, and high are available, the size of the observation field at a low magnification used for detecting a defect within the field). Therefore, in the case of a large foreign matter having a considerable area, a defect may be detected on a plurality of cells on the reticle 1. When the foreign matter is attached near the boundary between neighboring cells, it may be detected at the two neighboring cells, and the same defect ranks may be displayed for the neighboring cells.

In the conventional defect inspection apparatus comprising the observation unit, defect detection by means of light beam scanning and observation of defect portions using the observation unit 15 are performed. However, the defect detection by means of light beam scanning and observation of defect portions cannot be simultaneously performed. The two main reasons therefor are as follows:

(i) Although the defect detection is performed by an oblique incident method for obliquely irradiating the light beam L2, as shown in FIG. 7, the observation of defect portions using the observation unit 15 is attained by vertical irradiation or transmission illumination. For this reason, a common light source cannot be used for these two modes.

(ii) In the defect detection, light other than very weak scattered light from a defect such as a foreign matter disturbs inspection. For this reason, when the observation unit 15 is arranged near the scanning line 10, the oblique incident beam (light beam L2) or scattered light of the light beam L2 from the surface of the reticle 1 is irradiated onto the observation unit 15 and excessive light is generated. Therefore, the observation unit and the defect detection unit must be arranged to be separated away from each other.

As described above, in the conventional defect detection apparatus, the detect detection and the observation of defect portions cannot be simultaneously performed, and the defect detection by means of light beam scanning is performed at high speed upon scanning of the galvano mirror 6 and movement of the stage 2. Therefore, most of the inspection time is a defect observation time using the observation unit 15, and in order to shorten the time required for the inspection process, the defect observation using the observation unit 15 must be performed quickly. However, the conventional inspection method merely allows observation of detected defects in the order of, e.g., detection on the reticle 1, and does not sufficiently consider means for shortening the time required for the inspection process.

SUMMARY OF THE INVENTION

In accordance with the first aspect of the present invention, the present invention has as an object to provide a defect inspection method, which performs defect detection by dividing a surface to be inspected into a plurality of cells, and can accurately determine a single defect even when a single defect larger than each cell size is present or when a single defect is present near a boundary between neighboring cells.

According to the present invention, in a defect inspection method for irradiating inspection light onto a surface to be inspected of an object to be inspected, which surface is divided into a plurality of imaginary cells at predetermined pitches in both a first direction (X direction) and a second direction (Y direction) perpendicular to the first direction, assigning a defect signal to each of cells on which a defect is located on the basis of the magnitude of a photoelectric signal obtained by photoelectrically converting scattered light from the defect on the surface to be inspected, and displaying the defect signal as a defect inspection result of the surface to be inspected: when defect signals are assigned to a plurality of cells which neighbor in at least one of the first direction (X direction) and the second direction (Y direction), only a maximum one of the defect signals assigned to the plurality of neighboring cells is displayed as the defect inspection result.

In this case, a maximum one of defect signals in N×M cells consisting of N (N is an integer equal to or larger than 2) cells in the first direction (X direction) and M (M is an integer equal to or larger than 2) cells in the second direction (Y direction) may be left.

Alternatively, the N×M cells may be scanned in the first direction (X direction) and the second direction (Y direction) to leave maximum defect signals in the corresponding scanning directions.

It is preferable that the N×M cells be 2×2 cells.

When both defect signals of two cells on one diagonal line of the 2×2 cells are equal to or smaller than a predetermined detection threshold value, it is preferable that defect signals of two cells on the other diagonal line be left.

The present invention is achieved in consideration of the fact that the distribution density of defects such as foreign matters on the surface to be inspected is small (for example, on the reticle, one foreign matter may or may not be present in a 10-mm square) in the field to which the present invention is applied.

According to the present invention, when a large defect is present, and defect signals are obtained from three neighboring cells C1 to C3, as shown in FIG. 1B, a maximum defect signal "100" of the three neighboring cells C1 to C3 is left. Therefore, the defect signal "100" is finally left on only the cell C2, as shown in FIG. 2D, and a defect can be prevented from being detected from a plurality of cells.

The basic principle of leaving only a maximum defect signal lies in the fact that the defect detection is realized by executing, e.g., peak detection of a photoelectric signal obtained from the two-dimensional surface to be inspected. When the peak detection is performed, as described above, even a single defect having a wide area has only one peak corresponding to a maximum scattered light amount (photoelectric signal), and the cell corresponding to the maximum peak can be determined as a cell where the defect is present. Since the present invention assumes that the distribution density of defects is low, even when a plurality of defects are present at neighboring positions, these defects are present to be separated by one or a plurality of cells having no defect signals (having defect signals of 0) interposed therebetween. Therefore, when the present invention is applied, the plurality of defects can be independently detected.

Even when a single defect is present on the boundary portion between two neighboring cells, since a defect signal is left on either one of the cells, the defect can be identified as a single defect.

When the above-mentioned detection of a maximum defect signal is performed in the N×M cells, even a defect which has a size extending over the N×M cells can be efficiently detected as a single defect.

When the surface to be inspected is scanned using the N×M cells, a large defect can be detected as a single defect on the entire surface to be inspected. In addition, two defects, which are separated by an interval corresponding to (N-1) cells in the first direction or by an interval corresponding to (M-1) cells in the second direction can be determined as different defects.

If the N×M cells are assumed to be 2×2 cells, two defects which are separated by an interval of one cell in the first or second direction can be determined as different defects, and the resolution of the defect detection can be improved.

When both defect signals on two cells on one diagonal line of the 2×2 cells are equal to or smaller than a predetermined detection threshold value, defect signals on two cells on the other diagonal line are left. In this case, as shown in, e.g., FIG. 4, even when different defects are present on two obliquely neighboring cells C7 and C8, defect signals "100" and "70" are left after processing, as shown in FIG. 6. Therefore, defects on two obliquely neighboring cells can be determined as different defects, and the resolution of the defect detection can be improved.

In accordance with the another aspect, the present invention has as an object to provide a defect inspection method which executes defect detection and defect observation, and can shorten the inspection time. The present invention also has as an object to provide a defect inspection apparatus which can carry out this defect inspection method.

In one defect inspection method according to the present invention in which inspection light is irradiated onto the surface to be inspected of an object to be inspected, a defect on the surface to be inspected is detected on the basis of scattered light of the inspection light from the surface to be inspected, and the detected defect is observed at a predetermined magnification: the size of the defect on the surface to be inspected is determined on the basis of a photoelectric conversion signal V of the scattered light of the inspection light from the surface to be inspected; when a plurality of defects are detected, the detected defects are observed in the order from larger defects at the predetermined magnification; and when a defective portion is found as a result of the observation, defect inspection of the object to be inspected is terminated.

According to the defect inspection method, the sizes of defects are determined upon detection of defects such as foreign matters on the surface to be inspected, and thereafter, when defects on the surface to be inspected are observed at the predetermined magnification, they are observed in the order from larger ones. When a defective portion is found, the defect inspection of the object to be inspected is terminated, thus shortening the inspection time. If the object to be inspected is, e.g., a reticle, an example of the defective portion is a light-transmitting portion of the reticle to which a foreign matter beyond a predetermined standard is attached.

In another defect inspection method according to the present invention in which inspection light is irradiated onto the surface to be inspected of an object to be inspected, a defect on the surface to be inspected is detected on the basis of scattered light of the inspection light from the surface to be inspected, and the detected defect is observed at a predetermined magnification: the surface to be inspected is divided into a plurality of cells each having a predetermined size; the sizes of maximum defects in the plurality of cells are determined on the basis of a photoelectric conversion signal V of the scattered light of the inspection light from the surface to be inspected; the cells including defects of the plurality of cells are observed in the order from larger maximum defects therein on the basis of the determination result; and when a defective portion is found as a result of observation, defect inspection of the object to be inspected is terminated.

According to this defect inspection method, the surface to be inspected is divided into a plurality of cells (a large number of small regions arranged very close to each other), maximum defects are detected in units of cells, and the defects are observed in the order from the cells including larger maximum defects. When a defective portion is found, the defect inspection of the object to be inspected is terminated, thus shortening the inspection time. Since the maximum defects are extracted in units of cells, the inspection time can be shorter than that of the above-mentioned defect inspection method.

In still another defect inspection method according to the present invention in which inspection light is irradiated onto the surface to be inspected of an object to be inspected, and a defect on the surface to be inspected is detected on the basis of scattered light of the inspection light from the surface to be inspected: the size of a defect on the surface to be inspected is determined on the basis of a photoelectric conversion signal V of the scattered light of the inspection light from the surface to be inspected; and when at least one of a case wherein the number of detected defects has exceeded a predetermined allowable value and a case wherein the detected defects include a defect having a size exceeding a predetermined allowable value occurs, the defect inspection of the object to be inspected is terminated.

According to this defect inspection method, when the number of defects has already exceeded the allowable value or when a defect having a size exceeding the allowable value is detected in the defect detection process before observation, the object to be inspected is determined as a defective one, and the inspection is terminated without executing observation even in the middle of the defect inspection. Thus, the inspection time can be shortened.

Each of first and second defect inspection apparatuses according to the present invention comprises light scanning means for scanning inspection light on the surface to be inspected of an object to be inspected, scanning position measurement means for measuring the scanning position of the inspection light on the surface to be inspected, light-receiving means for photoelectrically converting scattered light of the inspection light from the surface to be inspected, and observation means for observing the surface to be inspected at a predetermined magnification, wherein a defect on the surface to be inspected and the position of the defect are detected on the basis of the output signals from the light-receiving means and the scanning position measurement means, and the detected defect is observed by the observation means.

The first defect inspection apparatus further comprises defect determination means for determining the size of a defect on the surface to be inspected on the basis of an output signal V from the light-receiving means, storage means for storing the sizes and positions, on the surface to be inspected, of the defects in units of defects on the surface to be inspected on the basis of the determination result from the defect determination means and the output signal from the scanning position measurement means, and control means for controlling the positional relationship between the object to be inspected and the observation means on the basis of the sizes and positions, on the surface to be inspected, of defects stored in the storage means so that the defects can be observed in the order from larger defects.

On the other hand, the second defect inspection apparatus further comprises defect determination means for determining the size of a defect on the surface to be inspected on the basis of an output signal from the light-receiving means, storage means for dividing the surface to be inspected into a plurality of imaginary cells each having a predetermined size, and storing sizes of maximum defects in the cells and positions of the cells on the surface to be inspected in units of cells having defects of the plurality of cells, and control means for controlling the positional relationship between the object to be inspected and the observation means on the basis of the sizes of the defects and the positions of the cells on the surface to be inspected stored in the storage means so that the defects can be observed in the order from larger defects.

A third defect inspection apparatus of the present invention, which includes light scanning means for scanning inspection light on the surface to be inspected of an object to be inspected, scanning position measurement means for measuring the scanning position of the inspection light on the surface to be inspected, and light-receiving means for photoelectrically converting scattered light of the inspection light from the surface to be inspected, and which apparatus detects a defect on the surface to be inspected and its position on the basis of the output signals from the light-receiving means and the scanning position measurement means, comprises defect determination means for determining the size of a defect on the surface to be inspected on the basis of the output signal from the light-receiving means, storage means for storing sizes and positions, on the surface to be inspected, of defects in units of defects on the surface to be inspected, first comparison means for comparing the number of defects stored in the storage means with a predetermined allowable value, and second comparison means for comparing the size of a maximum one of the defects stored in the storage means with another predetermined allowable value.

DETAILED DESCRIPTION OF THE PREFERRED EMBODIMENTS

The first embodiment of the present invention will be described below.

Figure 7:
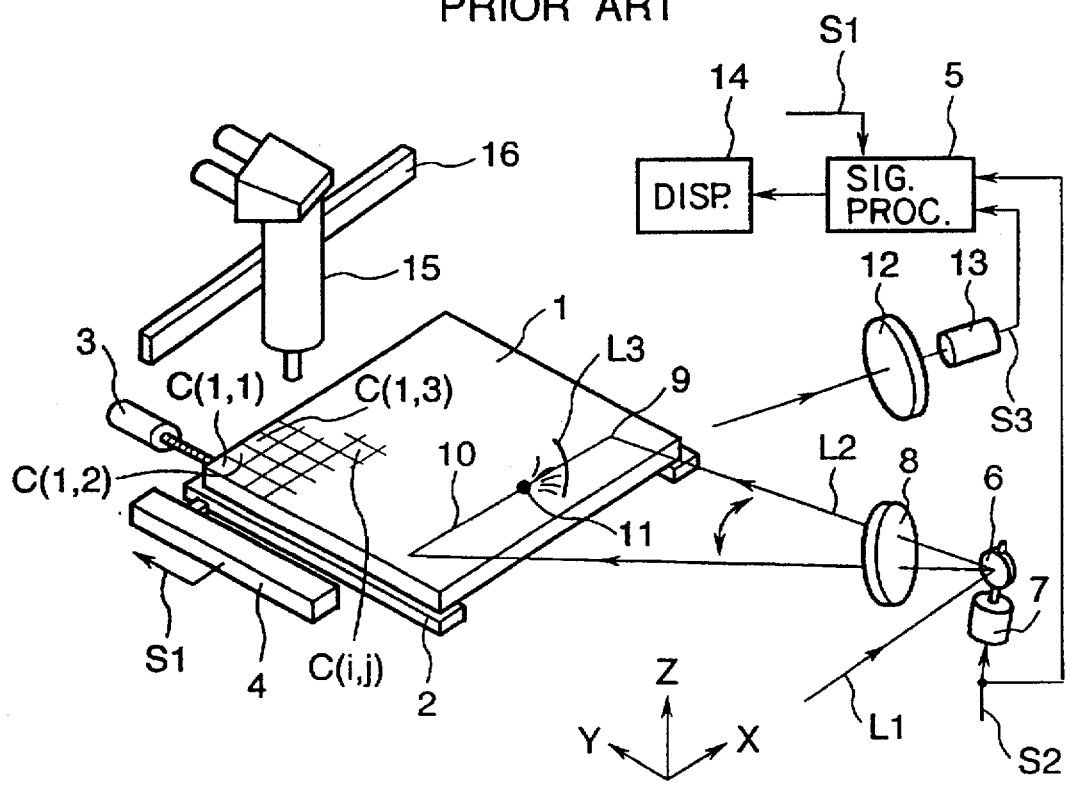
FIG. 7 is a diagram, including a partial perspective view, showing the arrangement of an example of a conventional defect inspection apparatus.
Figure 11:
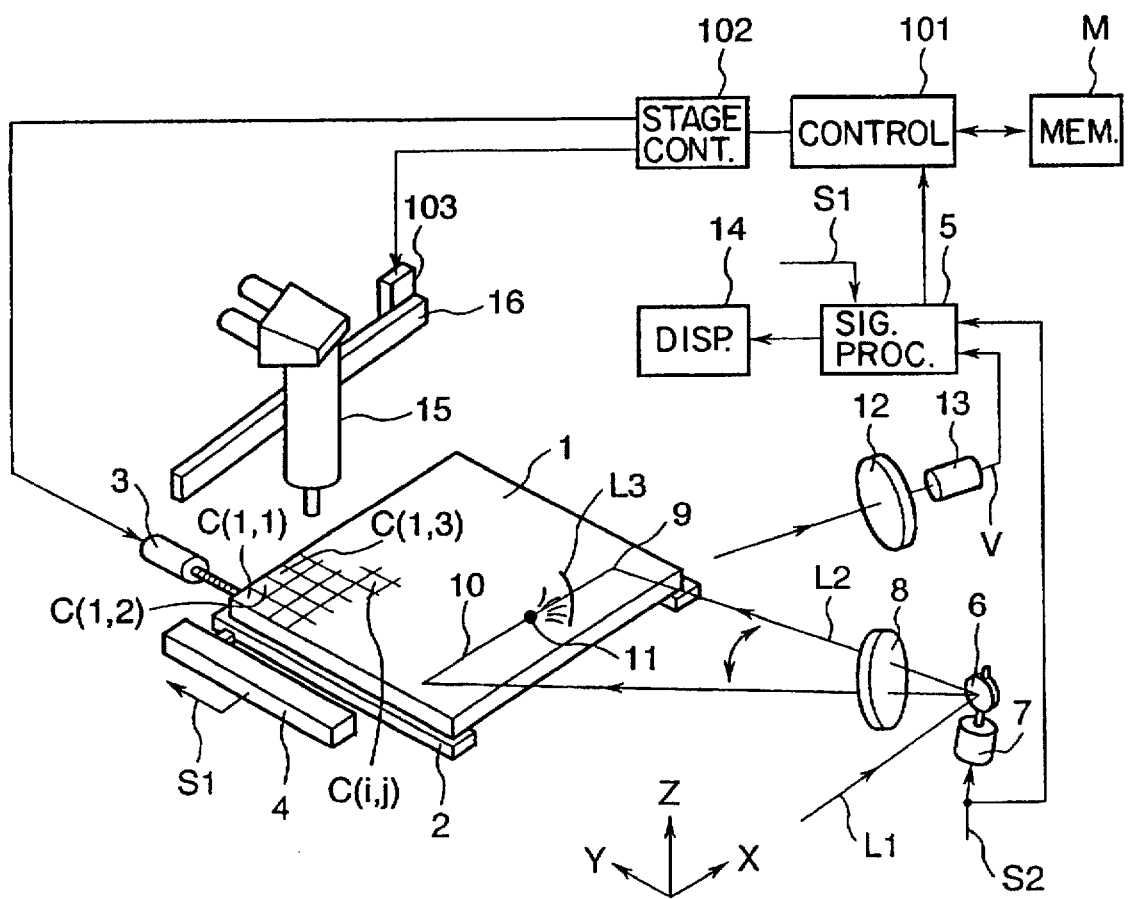
FIG. 11 is a schematic diagram, including a partial perspective view, showing the arrangement of a defect inspection apparatus according to the first embodiment of the present invention.

FIG. 11 shows a defect inspection apparatus according to this embodiment. The same reference numerals in FIG. 11 denote the same parts as in FIG. 7, and a detailed description thereof will be omitted. Referring to FIG. 11, a detection signal V output from photoelectric detector 13 is supplied to a signal processing circuit 5. When the peak value of the detection signal V exceeds, e.g., a predetermined threshold value, the signal processing circuit 5 determines a defect. The signal processing circuit 5 also receives a position signal S1 from a distance measurement device 4 and a deflection angle signal S2 for a driving unit 7 of a galvano scanner 6, and can recognize the X- and Y-coordinates of the defect detected by the signal processing circuit 5. The signal processing circuit 5 outputs a defect detection signal V and a position signal S1 of a foreign matter to a main control system 101. The main control system 101 is connected to a memory M for storing the positions and sizes of defects. A driving unit 103 for driving an observation unit 15 in the X direction is provided on a slider 16. The main control system 101 controls the operations of a driving unit 3 and the driving unit 103 via a stage driving unit 102 to set a desired position, in the Y direction, of a stage 2, and to set a desired position, in the X direction, of the observation unit 15. Thus, a desired region on a reticle 1 can be quickly set within the observation region of the observation unit 15. In the apparatus shown in FIG. 11, scattered light obtained by scanning the entire surface of the reticle with a light beam L2 is photoelectrically converted to obtain the detection signal V. As shown in FIG. 11, the surface of the reticle 1 is partitioned at predetermined pitches in both the X and Y directions to be divided into a large number of cells $C(i, j)$ ($i=1, 2, \ldots ; j=1, 2, \ldots$), and a maximum value of a detection signal V in each cell is determined as a detection signal in the corresponding cell. In this case, a detection threshold value is set to be "50" in consideration of the noise level of the detection signal V, and it is determined that a detection signal V equal to or smaller than the detection threshold value is not a defect. More specifically, all detection signals V equal to or smaller than the detection threshold value are set to be "0". Detection signals obtained after signals equal to or smaller than the detection threshold value are converted into "0" will be referred to as defect signals hereinafter.

Figure 1A:
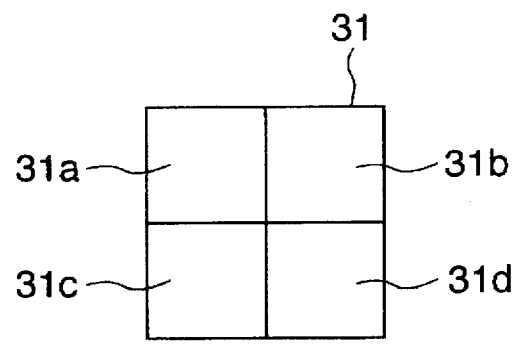
FIG. 1A is a view showing a logic matrix according to the first embodiment of the present invention.
Figure 1A:
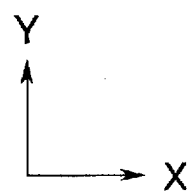
Figure 1B:
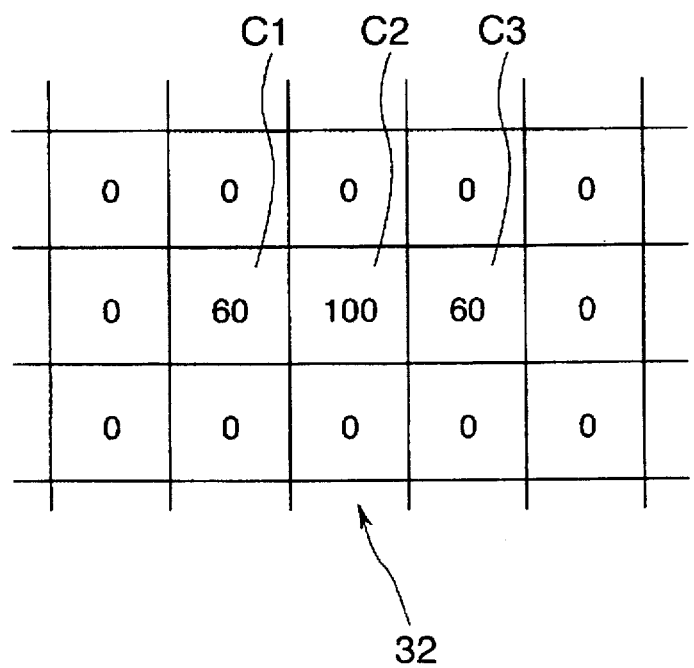
FIG. 1B is a view showing an example of an object to be processed in the first embodiment.

A case will be examined below wherein detection data (initial data) shown in FIG. 1B are obtained as a result of assignment of defect signals to the cells on the reticle 1. FIG. 1B shows only a partial region 32 of the inspection map on the entire surface of the reticle 1. In FIG. 1B, defect signals "60", "100", and "60" are respectively assigned to three continuous cells C1 to C3 in the X direction, and defect signals "0" are assigned to other cells, i.e., detection signals of other cells are equal to or smaller than the detection threshold value.

In this embodiment, as shown in FIG. 1A, a selection block (to be referred to as a "logic matrix" hereinafter) 31 having a 2×2 cell size (two cells in the X direction and two cells in the Y direction) is used. The logic matrix 31 has a logic of leaving only a maximum defect signal in a total of four cells 31a to 31d, and removing other defect signals (setting them to be "0"). All cells in the partial region 32 shown in FIG. 1B are sequentially scanned with the logic matrix 31. FIGS. 2A to 2D show the scanning state. Note that each of FIGS. 1A and 1B and the subsequent drawings illustrates a state wherein detection signals are assigned to cells on the reticle 1. However, in practice, detection signals are stored at addresses in the memory M, which correspond to the cells, and the following processing using the logic matrix 31 is executed in a software manner in the memory M. Furthermore, the intermediate results of the processing may be displayed on display cells, corresponding to the cells on the reticle 1, on the screen of a display device.

As shown in FIGS. 2A to 2D, the logic matrix 31 is shifted (scanned) cell by cell on first and second rows 33A and 33B of the partial region 32. In the state shown in FIG. 2A, since only a cell C1 has a defect signal other than "0" in the logic matrix 31, the maximum value of the defect signal is "60" of the cell C1, as a matter of course. Then, in the state shown in FIG. 2B, defect signals other than cells C1 and C2 are "0". When the defect signals Of the cells C1 and C2 are compared with each other, since the defect signal of the cell C2 is larger than that of the cell C1, the defect signal of the cell C1 is removed, and only the defect signal of the cell C2 is left.

Figure 2A:
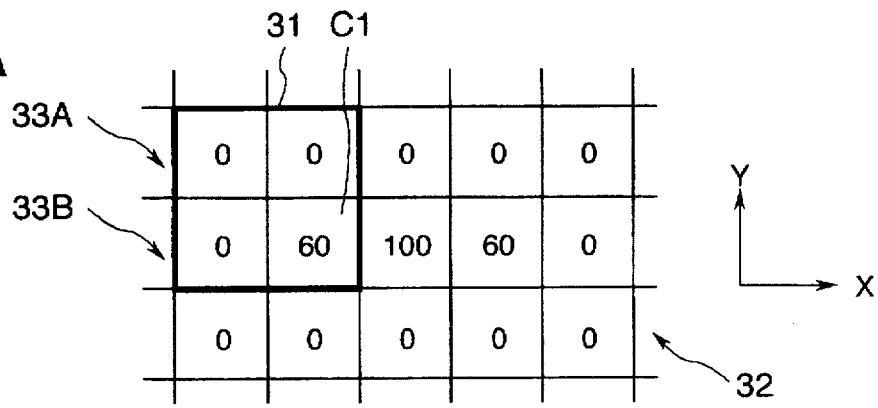
FIGS. 2A to 2D are explanatory views of an operation for performing processing of the logic matrix shown in FIG. 1A for the object to be processed shown in FIG. 1B.
Figure 2B:
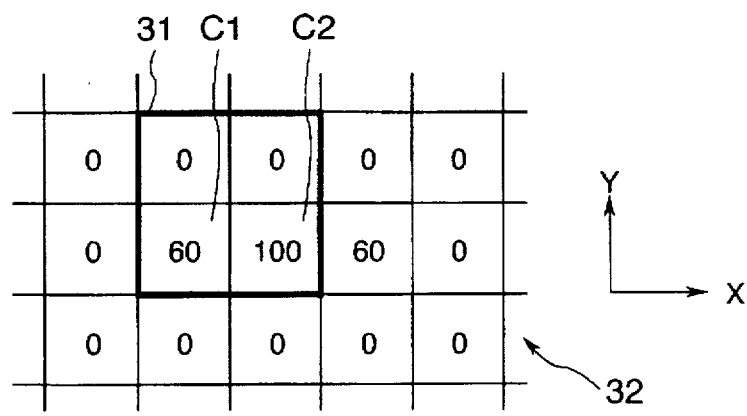
Figure 2C:
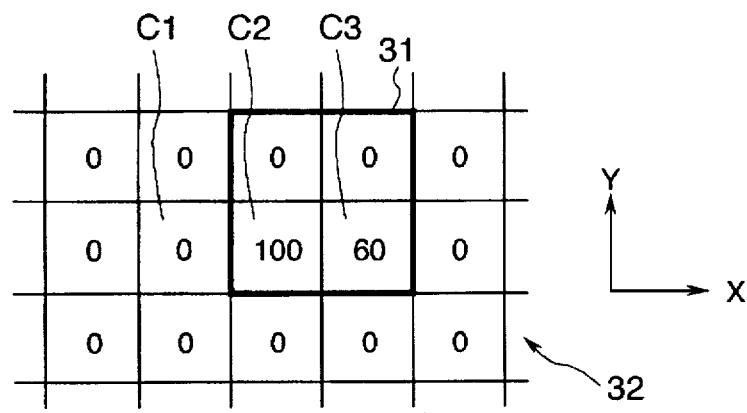
Figure 2D:
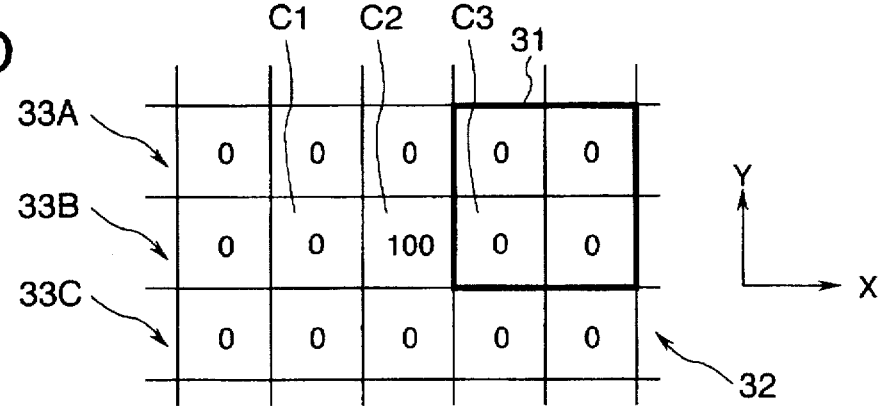

In the state shown in FIG. 2C, since the defect signal of the cell C2 has already been removed in the state of. FIG. 2B, the defect signal of the cell C1 is "0". Upon comparison between cells C2 and C3 in the logic matrix 31, since the defect signal of the cell C2 has a larger value than that of the defect signal of the cell C3, the defect signal of the cell C3 is removed. When the logic matrix 31 is set, as shown in FIG. 2D, since the defect signal of the cell C3 has already been removed in the state in FIG. 2C, all defect signals in the logic matrix 31 are "0", and hence, the maximum value in the logic matrix 31 is also "0". With the above-mentioned processing, of the defect signals in the partial region 32 shown in FIG. 1B, the defect signals of the cells C1 and C3 are removed (set to be "0"), only the defect signal having a value "100" of the cell C2 is left, and the defect signal value of the cell C2 and its position are left as defect data. The same processing is performed even when the logic matrix 31 is shifted to the next row in the partial region 32, but the defect signal of the cell C2 is left.

When the logic matrix 31 is sequentially two-dimensionally set (scanned) to a first defect signal group (data including a case wherein defects are displayed on continuous cells) obtained by inspecting the entire surface of the reticle 1, only a maximum defect signal in continuous cells in the X or Y direction is left. The finally left defect signal is displayed on, e.g., a CRT display as defect data in the form of a map. Parallel to this operation, the defect position and the value of the defect signal are output in the form of a table. With this processing, even when a defect larger than a single cell is present on the reticle 1, or even when a single small defect is present on the boundary portion between neighboring cells, such a cell can be accurately identified as a single defect.

Figure 3A:
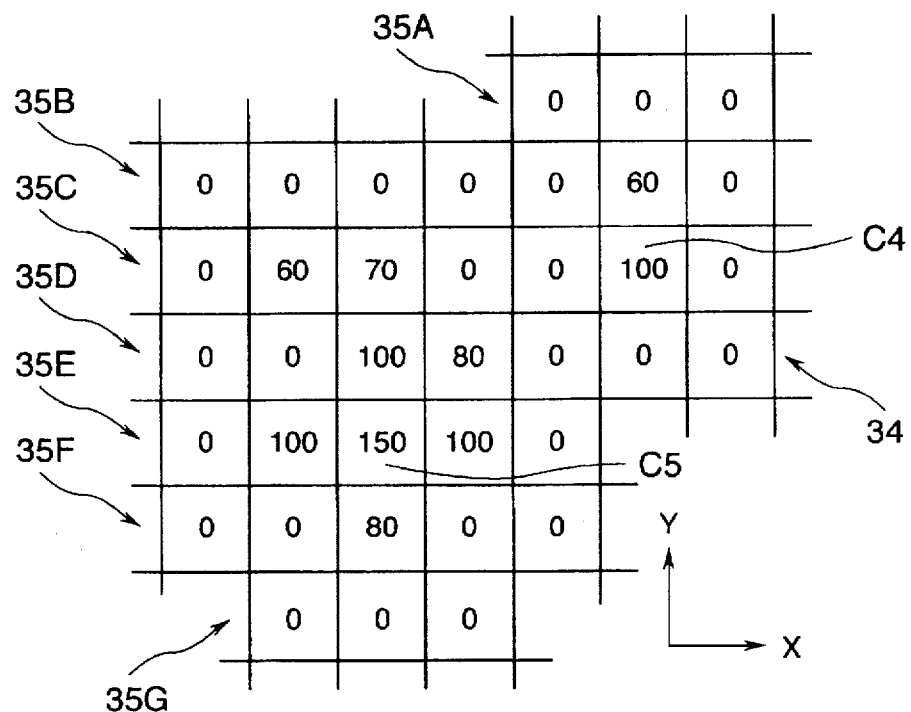
FIG. 3A is a view showing another object to be processed in the first embodiment.

The above-mentioned method is applied to a case wherein large defects are present to be separated by predetermined intervals, as shown in FIG. 3A. FIG. 3A shows the distribution of defect signals obtained when a partial region 34 on the reticle is divided into a large number of cells. First, on first and second rows 35A and 35B in this partial region 34, the logic matrix 31 in FIG. 1A is scanned in the X direction to leave only a maximum defect signal. Then, on the second row 35B and a third row 35C, the logic matrix 31 is scanned in the X direction. This operation is sequentially repeated, and finally on sixth and seventh rows 35F and 35G, the logic matrix 31 is scanned in the X direction to leave only a maximum defect signal.

Figure 3B:
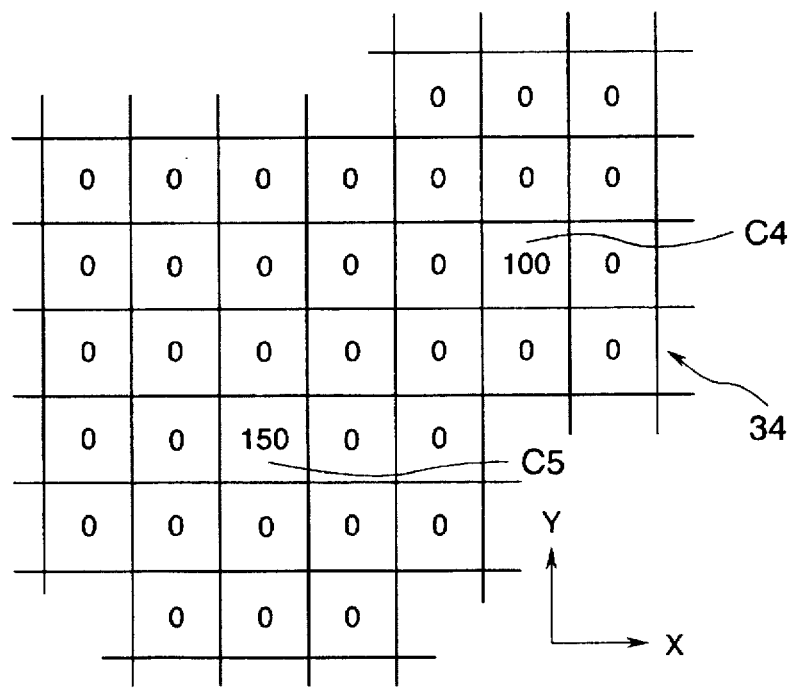
FIG. 3B is a view showing the processing result of the logic matrix shown in FIG. 1A for the object to be processed shown in FIG. 3A.

As a result, as shown in FIG. 3B, only a defect signal with a value "100" of a cell C4 and a defect signal with a value "150" of a cell C5 are left as defect data. Therefore, according to this embodiment, when different defects are present in distant cells, they dan be determined as independent defects.

Figure 4:
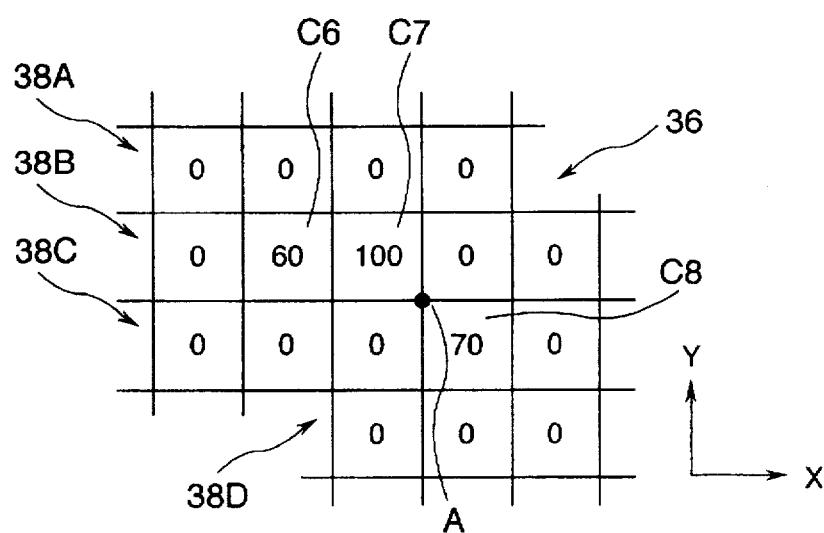
FIG. 4 is a view showing the distribution of defect signals obtained when different defects are present on obliquely neighboring cells.

However, with only the above-mentioned method, a problem is posed in the case of FIG. 4. More specifically, FIG. 4 shows the distribution of defect signals in a partial region 36 on the reticle. When the logic matrix 31 shown in FIG. 1A is set on second and third rows 38B and 38C in this partial region 36, only a defect signal of a cell C7 is left as defect data. However, in practice, FIG. 4 illustrates that a relatively large foreign matter is present on the cell C7, and a relatively small foreign matter is present on a cell C8 which neighbors the cell C7 at a point A in the oblique direction. This is because the two-dimensional peaks of defect signals are present on the cells C7 and C8 in FIG. 4, and defect signals of two neighboring cells at the point A in a direction different from the neighboring direction of the cells C7 and C8 are "0".

Figure 5:
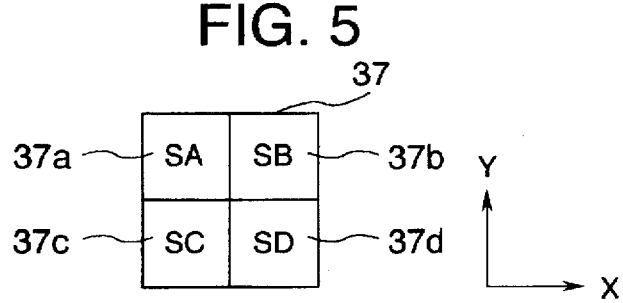
FIG. 5 is a view showing a logic matrix according to a modification of the first embodiment of the present invention.

For this reason, a logic matrix 37 shown in FIG. 5 as a modification will be examined below. The logic matrix 37 of this modification also consists of a total of four cells 37a to 37d (two cells in the X direction and two cells in the Y direction). In this modification, when diagonal components of defect signals in the logic matrix 37 are "0", maximum value selection is not performed. More specifically, if defect signals of the cells 37a, 37b, 37c, and 37d are respectively represented by SA, SB, SC, and SD, when SA=0 and SD=0, or when SB=0 and SC=0 (they may be rewritten as SA+SD=0 or SB+SC=0), defect signals other than "0" of other cells are left as defect data. When SA+SD=0 or SB+SC=0 is not established, only a maximum defect signal in the matrix is left as in the first embodiment.

Figure 6:
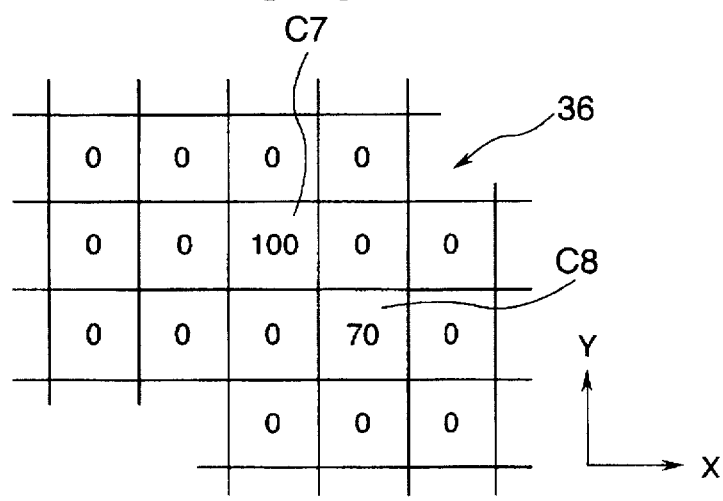
FIG. 6 is a view showing the processing result of the logic matrix shown in FIG. 5 for the object to be processed shown in FIG. 4.

As can be seen from FIG. 6, when the second and third rows 38B and 38C in the partial region 36 in FIG. 4 are scanned by this logic matrix 37, defect signals of the cells C7 and C8 are left, and different defects on obliquely neighboring cells are determined as independent defects.

Upon application of the method of the above embodiment, if defect signals are obtained by dividing, e.g., a 100 (mm)×100 (mm) inspection region on the reticle into 1-mm square cells, there are a total of 10,000 cells. When the logic matrix 31 (or 37) consisting of 2×2 cells is sequentially set for all these cells, a considerably long processing time is required. More specifically, the processing time can be shortened by ignoring portions where defect signals of all four cells (e.g., the four cells 37a to 37d in FIG. 5) in the logic matrix 31 (or 37) are "0". Thus, it is preferable to arrange means for selecting cells to set the logic matrix 31 (or 37) to only the first cell which is determined to include a defect such as a foreign matter. In this case, if there is no foreign matter although it may seem an extreme case, this state is directly stored as defect data (the data indicating no defect) without setting the logic matrix.

Note that removal of defect signals using the logic matrix 31 (or 37) may be performed for data read out from a storage unit after the entire surface of the reticle 1 has been scanned with a light beam, but may be performed simultaneously with the scanning of the light beam each time inspection ends in units of cells.

In the above-mentioned embodiment, the 2×2 logic matrix is used. The logic matrix can be easily expanded to one consisting of N cells in the X direction and M cells in the Y direction.

In the above-mentioned apparatus, since a maximum defect signal of those of neighboring cells is left, even when a large defect is present or when a defect is present at the boundary portion between neighboring cells, such a defect can be determined as a single defect.

When a maximum defect signal in those of N×M cells is left, a defect as large as the total size of the N×M cells can be efficiently determined as a single defect.

When the N×M cells are scanned in the first and second directions and a maximum defect signal therein is left, defect detection can be efficiently performed on the entire surface to be inspected.

When the N×M cells are 2×2 cells, two defects which are present with one cell interposed therebetween can be determined as independent defects, and the detection resolution of defects can be improved.

In a case wherein when both defect signals of two cells on one diagonal line of the 2×2 cells are equal to or smaller than a predetermined detection threshold value, if defect signals of two cells on the other diagonal line are left, different defects present on obliquely neighboring cells can be identified as independent defects.

An embodiment according to the second aspect of the present invention will be described hereinafter.

The second embodiment will be described below with reference to FIGS. 12 to 14B. In this embodiment, the present invention is applied to a case wherein defect inspection of a reticle 1 (including one on which a pellicle is formed) is performed. The same reference numerals in FIG. 12 denote the same parts as in FIG. 7, and a detailed description thereof will be omitted.

Figure 12:
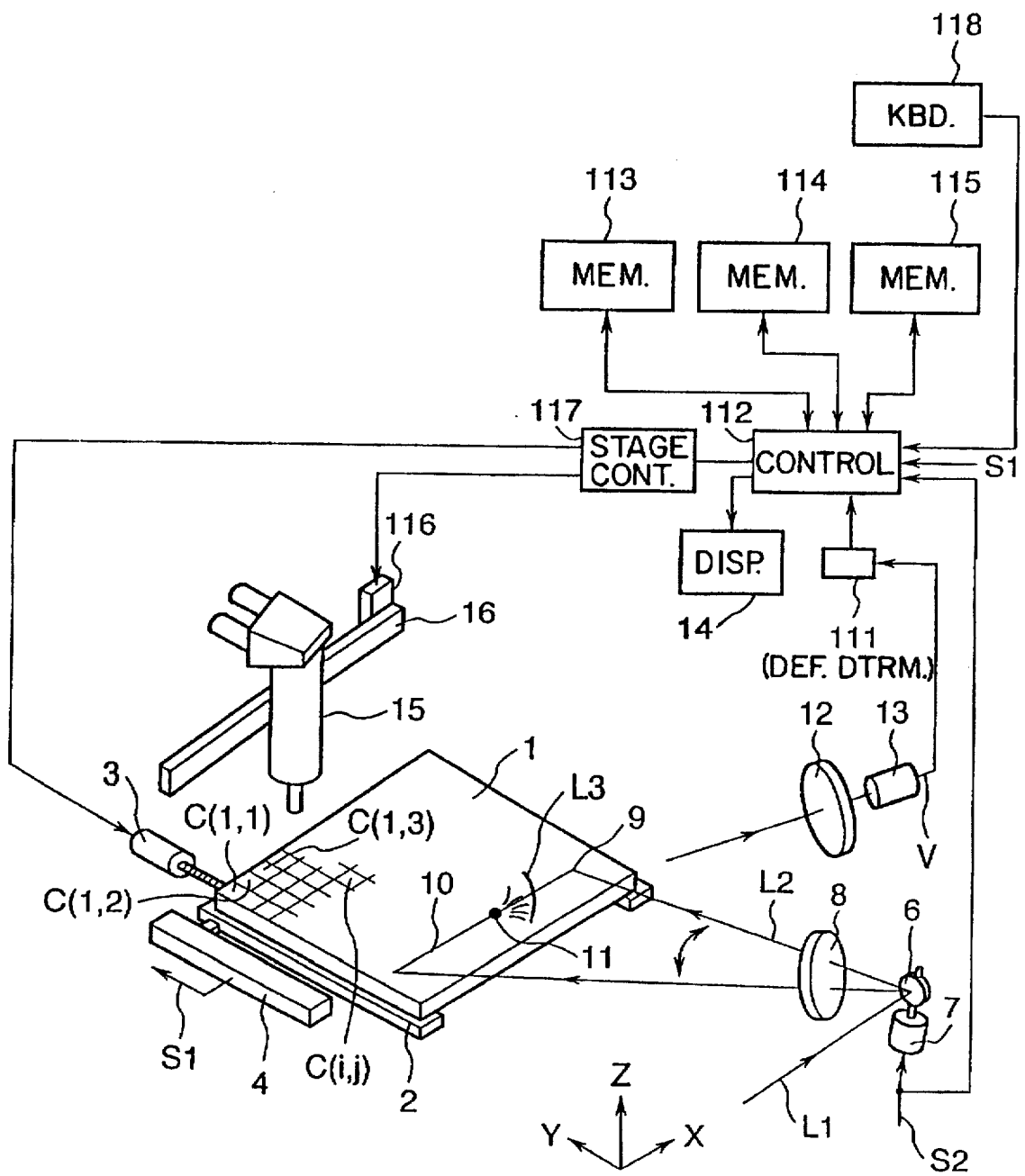
FIG. 12 is a schematic diagram, including a partial perspective view, showing the arrangement of a defect inspection apparatus according to the second embodiment of the present invention.

FIG. 12 shows a defect inspection apparatus of this embodiment. Referring to FIG. 12, a detection signal V output from a photoelectric detector 13 is supplied to a defect determination circuit 111. The defect determination circuit 111 determines a defect when the peak value of the detection signal V exceeds, e.g., a predetermined threshold value, and supplies a determination signal indicating a defect and a sample value $V_i$ (i=1, 2, . . . ) of the detection signal V at the defect portion to a main control system 112. The main control system 112 also receives a position signal S1 from a distance measurement device 4 and a deflection angle signal S2 for a driving unit 7 of a galvano scanner 6, and can recognize the X- and Y-coordinates of a defect detected by the defect determination circuit 111.

A driving unit 116 for driving an observation unit 15 in the X direction is provided on a slider 16, and the main control system 112 controls the operations of a driving unit 3 and the driving unit 116 via a stage control unit 117 to set a desired position, in the Y direction, of a stage 2, and to set a desired position, in the X direction, of the observation unit 15. Thus, a desired region on the reticle 1 can be quickly set within the observation region of the observation unit 15. Furthermore, the main control system 112 is connected to first, second, and third memories 113, 114, and 115, and a keyboard 118. An operator can input, e.g., commands indicating the start and end of defect inspection of the reticle 1 to the main control system 112 via the keyboard 118. The first and second memories, 113 and 114 store information indicating the sizes and positions of detected defects, as will be described later, and the third memory 115 stores various other data. Other arrangements are the same as those in FIG. 7.

The defect inspection operation of this embodiment will be described below with reference to FIG. 13 and FIGS. 14A and 14B. Referring to FIG. 12, the entire surface on the reticle 1 is scanned by a light beam L2, and the main control system 112 stores the coordinates (X, Y) of defects and sample values $V_i$ of the detection signal V upon detection of the defects by the defect determination circuit 111 in the first memory 113 in the order of detection.

Figures 13, 14A, 14B:
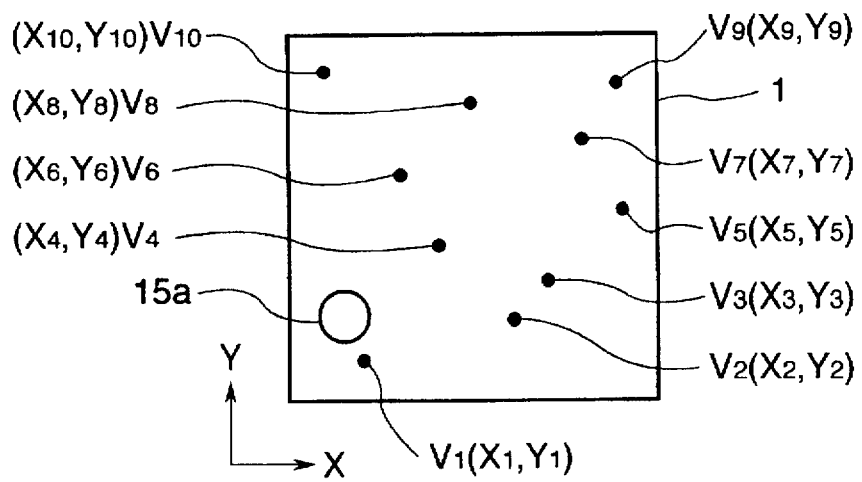
FIG. 13 is a plan view showing an example of the defect distribution on a reticle 1 in the second embodiment.
FIGS. 14A and 14B are views showing defect data respectively stored in first and second memories.

FIG. 13 shows an example Of the distribution of defects on the reticle 1. In FIG. 13, the X-coordinate is determined by the deflection angle signal S2 from the driving unit 7 of the galvano scanner 6 in FIG. 12, and the Y-coordinate is determined by the position signal S1 from the distance measurement device 4 in FIG. 12. In this example, defects with sample values $V_1, V_2, \ldots, V_{10}$ of the detection signal V are distributed at 10 coordinate positions $(X_1, Y_1), (X_2, Y_2), \ldots, (X_{10}, Y_{10})$ on the coordinates (X, Y) of the reticle 1. More specifically, since the values of the detection signal V at other coordinate positions are equal to or smaller than a predetermined threshold value determined in correspondence with the detection sensitivity, it is determined that no defects are present.

In this case, the coordinate position $(X_i, Y_i)$ (i=1 to 10) and the sample value $V_i$ of the detection signal V at this coordinate position are expressed together as data $(X_i, Y_i, V_i)$. The first memory 113 in FIG. 12 stores data $(X_1, Y_1, V_1)$ at the first address, stores data $(X_2, Y_2, V_2)$ at the second address, and stores data $(X_3, Y_3, V_3)$ to $(X_{10}, Y_{10}, V_{10})$ at the subsequent addresses in turn, as shown in FIG. 14A. After the end of light beam scanning of the entire surface of the reticle 1, the stored data are read out from the first memory 113, are sorted in the descending order of the sample values $V_1$ to $V_{10}$ of the detection signal, and are stored at serial addresses of the second memory 114 in FIG. 12 in the sorted order.

For example, if $V_4 > V_7 > V_2 > V_9 > \ldots$ as a result of sorting of the sample values $V_1$ to $V_{10}$ of the detection signal in the descending order, the second memory 114 in FIG. 12 stores data $(X_4, Y_4, V_4)$ at the first address, stores data $(X_7, Y_7, V_7)$ at the second address, and stores data $(X_2, Y_2, V_2), \ldots$ at the subsequent addresses, as shown in FIG. 14B. When data have the same sample value $V_i$, they may be stored in, e.g., the sampled order in the second memory 114. As a result, the second memory 114 stores the ordered data, and the order of the data is the descending order of the sample values $V_i$ of the detection signal.

Figure 8:
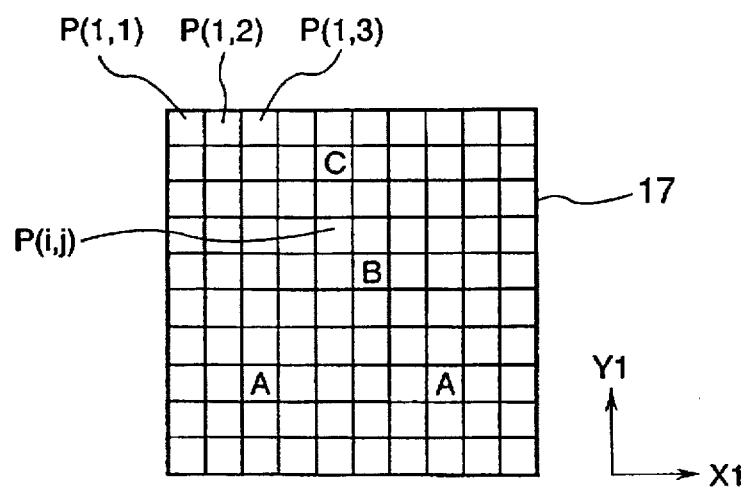
FIG. 8 is a view showing a display example of the defect detection result of the apparatus shown in FIG. 7 on a CRT display in the form of a map.
Figure 9:
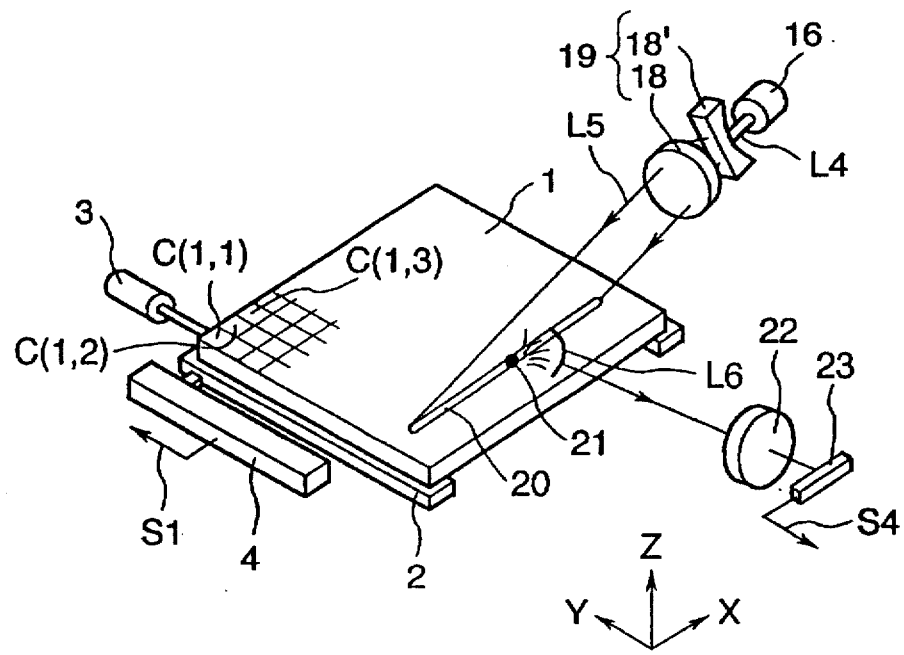
FIG. 9 is a diagram, including a partial perspective view, showing the arrangement of another example of a conventional defect inspection apparatus.
Figure 10:
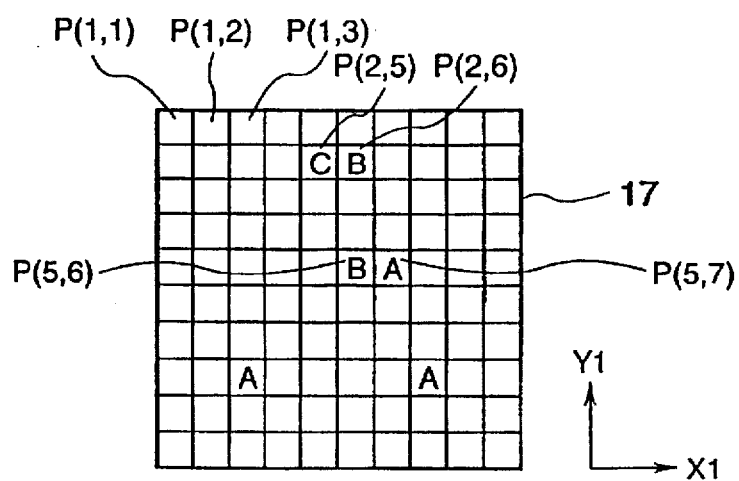
FIG. 10 is a view showing a display example of the defect detection result of the apparatus shown in FIG. 9 on a CRT display in the form of a map.

As has already been described above, as the detection signal V is larger, the defect size is larger. For this reason, the data in the second memory 14 are arranged in the descending order of the defect sizes. This order is not accurate if defects have already been classified into ranks indicated by symbols A, B, and C as in the prior art shown in FIG. 8. This is because defects may be classified into the same rank even if they have a signal difference therebetween. For this reason, in this embodiment, the sample value itself of the detection signal V is used.

Thereafter, the main control system 112 reads out the first (i.e., the largest size) defect data $(X_4, Y_4, V_4)$ from the first address of the second memory 114, and operates the driving units 3 and 116 to respectively move the reticle 1 and the observation unit 15, so that the center of the observation field of the observation unit 15 in FIG. 12 is set at the coordinate position $(X_4, Y_4)$. With this operation, in FIG. 13, the center of an observation field 15a of the observation unit 15 is set at the point of the coordinate position $(X_4, Y_4)$ on the reticle 1. An operator observes a defect at the coordinate position $(X_4, Y_4)$ visually or via an image observation system realized by a two-dimensional image pickup element (e.g., a CCD) attached to the observation unit 15 and a TV monitor.

As a result, when the operator determines that the defect has an allowable size, defect data $(X_7, Y_7, V_7)$ at the second address (the second largest size) of the second memory 114 is read out, and is similarly observed via the observation unit 15. The observation is performed in this manner since the value of the detection signal V does not always coincide with the actual size of a defect observed via the observation unit 15. In this case, when the defect having the largest size, which is observed first, has an allowable size, it can often be determined that defects having the second and subsequent sizes have allowable sizes. For this reason, when it is determined that the defect having the largest size has an allowable size, the corresponding reticle 1 may be handled as a good product without executing the subsequent observation operations, and the inspection process may be terminated. In this case, when the operator inputs an inspection end command to the main control system 112 via the keyboard 118 in FIG. 12, the reticle 1 is unloaded by a reticle loader system (not shown), and the next reticle to be inspected is set on the stage 2.

However, in practice, not only the size of a defect but also the attached position of a foreign matter as a defect serve as the criteria for defect determination. For example, in the case of a reticle, a foreign matter present on a light-transmitting portion poses a problem, but a foreign matter attached to a light-shielding portion consisting of a chromium film does not pose any problem since it is not transferred onto a wafer. If a defect of the first order is large but is located on the light-shielding portion of the reticle 1, the defect does not pose any problem. However, when a defect of the second order is located on a light-transmitting portion of the reticle 1, the reticle 1 may become a defective product. In this manner, as a result of observation of the defect of the second order, when the position of the defect corresponds to a light-transmitting portion of the reticle 1, the reticle may be determined as a defective product before defect data of the third order is read out from the second memory 114 and is observed via the observation unit 15, and the inspection process may be terminated.

Of course, upon observation of a defect such as a foreign matter of the first order, if the position of the defect corresponds to a light-transmitting portion of the reticle 1, the inspection process may be immediately terminated without continuing the remaining inspection process associated with the reticle 1. In this case, even if a defect is located on a light-transmitting portion of the reticle 1, when it has an allowable size after it is transferred onto a wafer, it is determined that the defect is negligible.

In place of arranging the first and second memories 113 and 114 in FIG. 12, the sample values $V_i$ of the detection signal V may be compared in the sampled order, and the sample values $V_i$ may be stored in predetermined storage portions after each comparison. Also, in place of sorting the detected data, only data indicating the descending order of defect sizes may be added to data which are arranged in the order of detection. With any method, defects are observed in the order of added data (or in the sorted order).

The third embodiment will be described below with reference to FIGS. 15A to 15C and FIGS. 16A and 16B. In this embodiment as well, defect inspection of a reticle is performed using the defect inspection apparatus shown in FIG. 12.

Figure 15A:
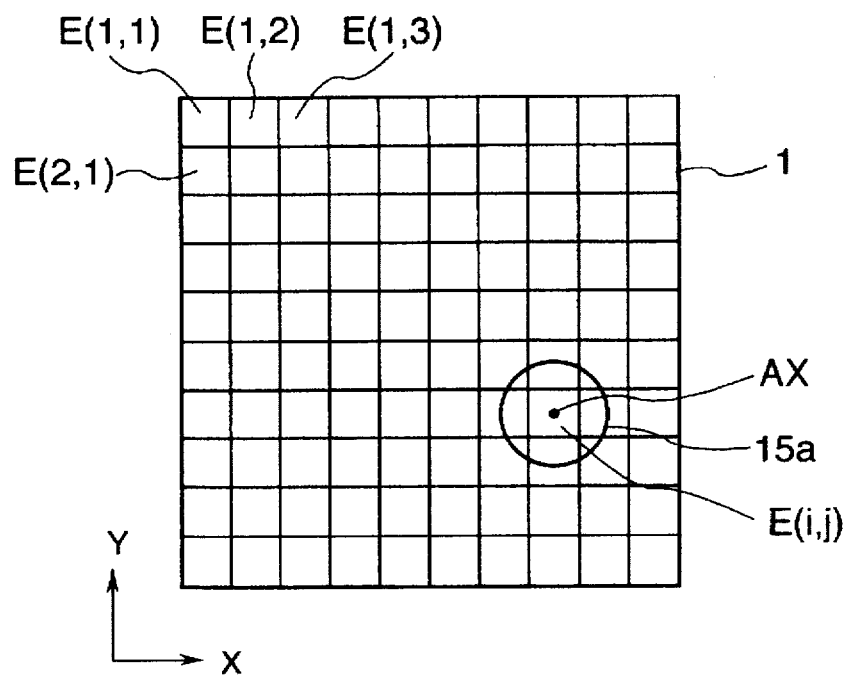
FIG. 15A is a plan view showing an example of divided cells on the reticle 1 in the second embodiment.
Figure 15B:
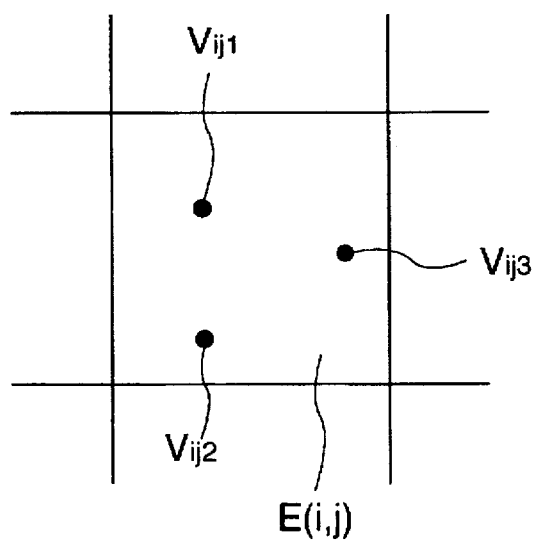
FIG. 15B is an enlarged plan view showing an example of the defect distribution in a cell E(i, j)

FIG. 15A shows a reticle 1 as an object to be inspected in this embodiment, assuming that the surface size of the reticle 1 is 100 mm×100 mm. Referring to FIG. 15A, the surface of the reticle 1 is partitioned at predetermined pitches in both the X and Y directions to be divided into cells E(1, 1), E(1, 2), . . . , E(2, 1), . . . as a large number of small rectangular regions, and data of defects are totalized in units of cells.

Originally, in the case of a reticle, the number of defects such as foreign matters is small, and one defect may or may not be present in a 10-mm square on the average. However, a plurality of foreign matters may be present at neighboring positions or may have different attached states (e.g., on a light-shielding portion, a light-transmitting portion, and the like). In order to observe neighboring foreign matters at a high resolution or to observe their attached states to determine whether or not a reticle is defective, a high observation magnification is required. In such a case, as shown in FIG. 15A, the size of each cell must be determined, so that the size of each cell E(i, j) (i=1, 2, . . . ; j=1, 2, . . . ) becomes smaller than that of the observation field 15a of the observation unit 15. Therefore, it is preferable that the cell size be 0.5- or 0.1-mm square.

Figure 15C:
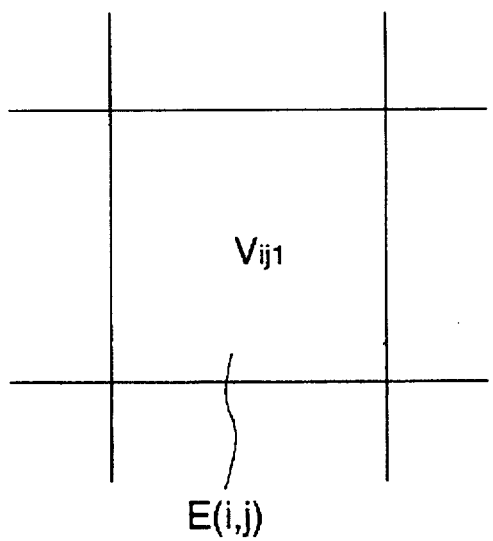
FIG. 15C is a view showing a defect detection signal assigned to the cell E(i, j)

In defect detection by scanning the light beam in this embodiment, when a plurality of defects are detected within a 0.5- or 0.1-mm square cell E(i, j) on the reticle 1, a defect having a larger sample value of the detection signal V is used as a representative sample value of the cell. More specifically, as shown in, e.g., FIG. 15B, if three defects having sample values $V_{ij1}$, $V_{ij2}$, and $V_{ij3}$ are present in the cell E(i, j), and a maximum one of the three sample values is $V_{ij1}$, $V_{ij}$ is assigned to the cell E(i, j) as a sample value of the detection signal indicating the defect, as shown in FIG. 15C. Then, the first memory 113 in FIG. 12 stores a central coordinate position $(X_{ij}, Y_{ij})$ of the cell and a sample value $V_{ij}$ of the detection signal of a maximum defect in the cell as data $(X_{ij}, Y_{ij}, V_{ij})$ in the order from cells from which defects are detected. At the same time, defects in the cells are classified into ranks A, B, C, and the like in correspondence with sample values, the number of defects in each rank is added in units of cells, and the sum is stored in the third memory 115.

Note that this method is effective for an apparatus which detects foreign matters by scanning a light beam on a reticle even if no observation unit 15 for foreign matters is arranged. More specifically, the spot size of the light beam on the reticle upon scanning of the light beam is larger than the size of a foreign matter, and the luminance of the light beam on the reticle has a Gaussian distribution (the luminance is high at the center of the beam and is lowered toward the peripheral portion). For this reason, the light beam is scanned, so that the skirt portion of the Gaussian distribution overlaps in neighboring scans. Normally, when the spot size of a beam having a Gaussian distribution is represented by W (a width which sets the luminance to be 13.5% of a peak value), the second scan is shifted from the first scan by about W/4 as a distance on the reticle. For this reason, scattered light signals are obtained from a single foreign matter in several beam scans, and these signals have different signal amounts depending on whether the center of the beam is irradiated onto the foreign matter or the skirt portion of the beam is irradiated onto it. Therefore, when the signal value and X- and Y-coordinate values are sampled each time a scattered light signal is obtained by scanning a light beam on the entire surface of the reticle, a plurality of pairs of neighboring X- and Y-coordinate values are sampled as data of a single foreign matter as if a plurality of foreign matters were present.

In order to solve this problem, the sampling unit cell size (data unit) is set to be a 0.1-mm square, and the maximum signal in each cell is used as a representative value of the cell.

This operation may be performed in a software manner, but it is preferable to perform this operation in a hardware manner. More specifically, a 0.1-mm square cell is used as a sampling unit cell, and when a defect signal is detected within the 0.1-mm square cell, the detected signal value is stored. If a defect signal larger than the stored defect signal is detected in the cell, the stored defect signal is erased and the signal value is updated. Finally, only the largest defect signal in the cell (0.1-mm square) is left, and this signal and the cell coordinate position are stored as data $(X_{ij}, Y_{ij}, V_{ij})$. $X_{ij}$ and $Y_{ij}$ represent the central coordinate position of the cell.

In order to display data on, e.g., a CRT display, the data is transferred. In this case, two transfer methods are available.

One transfer method is a method of transferring all data of the cells obtained by dividing the surface of the reticle. For example, when a 100 (mm)×100 (mm) region is transferred in units of 0.1-mm square cells, in accordance with a predetermined order (e.g., first to 100,000th addresses are predetermined from the upper left corner of the 100 (mm) ×100 (mm) region), data "0" is transferred when no foreign matter is detected, and a sample value $V_{ij}$ is transferred when a foreign matter is detected. When the transferred data are displayed, a display indicating no foreign matter is made in correspondence with the data "0", and a detection display ranked in correspondence with the sample value $V_{ij}$ is made. However, this method is not preferable since the data amount to be transferred becomes large.

The second method to be described below is more preferable. In this method, only detected data $(X_{ij}, Y_{ij}, V_{ij})$ are transferred, and a detection display is made on a corresponding cell in accordance with the coordinates $X_{ij}$ and $Y_{ij}$. This method is very effective since the number of transfer data is small when the number of foreign matters is small (normally, the number of foreign matters on a reticle is small), and since the transfer time can be shortened.

In this manner, upon completion of light beam scanning on the entire surface of the 100 (mm)×100 (mm) reticle 1, the main control system 112 in FIG. 12 displays the defect inspection result on a CRT display 14.

Figure 16A:
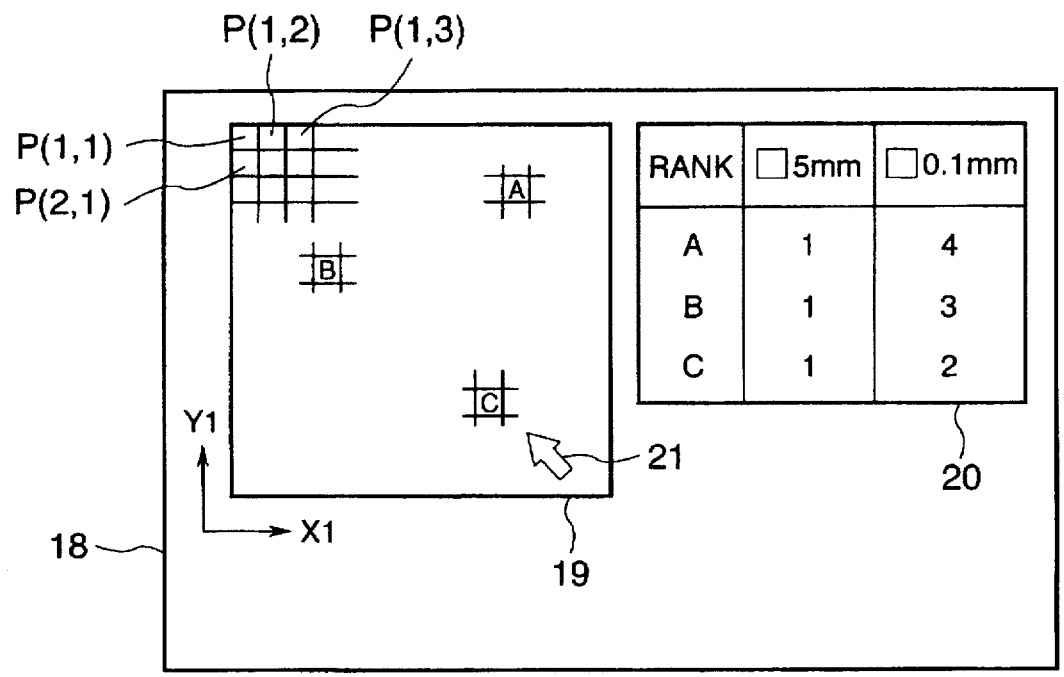
FIG. 16A is a view showing a portion of a defect display map in the second embodiment.
Figure 16B:
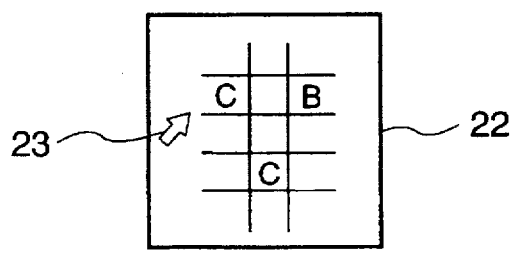
FIG. 16B is a view showing another portion of the display map.

FIG. 16A shows a display example on the CRT display 14. Referring to FIG. 16A, a window 19 in a large window 18 corresponds to the 100 (mm)×100 (mm) region of the reticle 1 shown in FIG. 15A. The window 19 is partitioned at predetermined pitches in an X1 direction corresponding to the X direction and a Y1 direction corresponding to the Y direction to be divided into a large number of display cells P(1, 1), P(1, 2), ..., P(2, 1), ..... On a display,cell, corresponding to a cell having a defect in FIG. 15A, of these display cells, a defect display which is ranked A, B, or C in correspondence with the sample value of a detection signal of the maximum defect in the corresponding cell is made in the form of a two-dimensional map.

In this case, even when the cell E(i, j) in FIG. 15A has a 0.1-mm square size, the display cell P(i, j) in FIG. 16A corresponds to a 5-mm square region on the reticle 1, and the window 19 is defined by a 20×20 matrix. Therefore, on each display cell P(i, j), the sample value of a detection signal of the maximum defect in the corresponding 5-mm square region on the reticle 1 is ranked and displayed. For this reason, since an accurate number of defects in units of 0.1-mm square cells is lost and unknown, the numbers of defects of ranks A, B, and C are displayed on a small window 20 beside the window 19 in two ways, i.e., in units of display cells (in units of 5-mm squares on the reticle 1) and in units of 0.1-mm square cells on the reticle 1.

Of course, in place of the defect size display using letters, defect sizes may be displayed on display cells in different colors (e.g., blue for a small size defect (foreign matter), green for a middle size, and red for a large size).

When defects in the cells on the reticle 1 are to be observed using the observation unit 15 in FIG. 12, the operator inputs an observation start command to the main control system 112 via the keyboard 118. In response to this command, the main control system 112 moves a cell of interest to the observation field 15a of the observation unit 15 on the basis of defect data in units of 0.1-mm square cells E(i, j) and in the descending order of maximum defects in the cells (in the order from larger defect sizes). The position of a defect which is being currently observed is indicated by an arrow cursor 21 in FIG. 16A. Furthermore, a defect display in units of 0.1-mm square cells on the reticle 1 is also made on a window 22 shown in FIG. 16B near the large window 18 on the display screen. In the window 22, in units of cells on the reticle 1 as well, an arrow cursor 23 indicates a cell which is being currently observed.

Furthermore, when defects are sequentially observed, it is preferable that an operator can know the progress of observation (the number of defects observed so far).

For example, observed cells may be deleted from the window 19 in FIG. 16A. When defects are observed in the descending order of sizes, a 5-mm square display cell of rank C may include two defects of rank C and one defect of rank B in units of 0.1-mm square display cells, as shown in, e.g., FIG. 16B. In this case, upon completion of observation of the two defects of rank C, since the display cell of rank C on the window 19 includes only one defect of rank B, its rank display is changed to rank B, and the display cells of rank C are deleted from the window 22 although the display cell having a defect is not deleted from the window 19. When all display cells having defects are deleted from the window 19, it indicates that all defects have been observed. In place of deleting displayed cells, the color of observed cells may be changed or observed cells may be blinked to be identifiable from unobserved cells. Alternatively, in place of deleting cells (or simultaneously with deletion of cells), the numbers of defects of ranks A, B, and C in units of 5-mm square cells and 0.1-mm square cells may be decremented in the order of observation to indicate the remaining numbers of defects of the respective ranks.

In place of the cursors 21 and 23, the current observation position may be indicated by a different color or by blinking the display. Alternatively, when defects are displayed or output in the form of a table in place of the display form shown in FIGS. 14A and 14B, a pattern indicating the observation position may be displayed or output near the table so as to be able to identify a defect which is being currently observed.

In this embodiment, in FIG. 15A, the cell E(i, j) on the reticle 1 may often include a plurality of defects having different sizes. In such a case, since the size of the cell is smaller than the observation field 15a of the observation unit 15 and the entire region in the cell can be observed via the single observation field 15a, a plurality of foreign matters can be simultaneously observed.

Of course, an observer cannot know the number of detected foreign matters in a cell of interest until he or she actually observes them. However, at the above-mentioned relatively high observation magnification, the observer can very easily find a plurality of foreign matters. At this time, the reticle 1 is moved relative to the observation field 15a on the basis of the central coordinate position of each cell E(i, j). More specifically, since the X- and Y-coordinates are determined in units of cells, the driving units 3 and 116 in FIG. 12 are controlled, so that the central coordinate position of the cell E(i, j) coincides with the center of the observation field 15a.

A series of defect inspection operations in this embodiment can be summarized in the following steps (i) to (vii).

(i) Defect detection is performed by scanning a light beam.

(ii) A maximum defect is determined in units of 0.1-mm square (or 0.5-mm square) cells.

(iii) Defect data are stored in the first memory 113 in units of cells.

(iv) The order of stored defect data is determined (from larger sizes) in correspondence with the defect sizes.

(v) A map display is made on the CRT display 14.

(vi) When an observation mode is designated, the center of the observation field is moved to the center of a corresponding cell in accordance with the order determined in step (iv).

(vii) Whether or not each defect is negligible is determined by visual observation or image observation. If a defect is not negligible, the following processing is interrupted.

In the above-mentioned steps, as the observation mode in step (vi), it is preferable if one of an automatic (auto) mode and a manual mode can be selected. For example, when the automatic mode is designated, defects are sequentially observed in the determined order; when the manual mode is designated, an operator designates a cell to be preferentially observed using a mouse or a cursor. After the cell is designated, the reticle 1 and the observation unit 15 are moved, so that the central coordinate position of the designated cell coincides with the center of the observation field 15a. The manual designation method is effective for a case wherein another neighboring defect is to be observed. In this sense, defects may be sequentially observed in a raster scan manner independently of the defect sizes.

The reticle 1 has a transfer region (pattern region), and defects such as foreign matters can be present on a region other than the transfer region. However, the transfer region does not always coincide with the defect inspection region. For example, in FIG. 15A, the transfer region has an 80 (mm)×90 (mm) size, but the inspection region is designated to have a 100 (mm)×100 (mm) size since a region as wide as possible is to be inspected in the inspection mode. However, since the presence/absence of defects in the transfer region of the reticle 1 is important in defect management, the observation using the observation unit 15 in FIG. 12 on the transfer region may be preferentially performed in some cases. In such a case, the priority may be assigned to the observation order, in such a manner that defects in the transfer region are selected first and are observed in the descending order of sizes using the observation unit 15, and thereafter, defects detected outside the transfer region are observed in the descending order of sizes using the observation unit 15.

As a modification of the above-mentioned embodiment, the size of the cell E(i, j) in FIG. 15A may be set to be relatively large (e.g., 5- or 1-mm square size), and in the map display, only the maximum sample value of a detection signal in each cell may be displayed as the representative value of the cell, as shown in the window 19 in FIG. 16A. In this case, as actual data, defect data are stored in units of central coordinates of smaller regions (e.g., 0.1-mm square) than the cells on the reticle 1 corresponding to the display cells in FIG. 16A, and defects are allowed to be observed in units of smaller regions upon designation by an operator.

As an application example of this modification, defect inspection based on an image processing method is known. In this image processing method, images on the entire surface of the reticle 1 are fetched as two-dimensional images using an image pickup device having a predetermined observation field (to be referred to as an "image field" hereinafter), and defects such as foreign matters are determined by image processing. Each image in the image field corresponds to each cell on the reticle 1 in FIG. 15A. The positions and sizes of defects in each image field are obtained, and when defects are to be observed in more detail, the observation field of the observation unit 15 is moved to the defect position in each image field at an observation magnification higher than that of the image field.

In addition, image data upon detection of a defect is stored in an image storage unit such as a frame memory. After the entire surface of the reticle 1 is scanned, the image data is read out from the image storage unit, and the image of the reticle 1 may be displayed on, e.g., a TV monitor. In this method, when a defect in the image field is to be observed at a higher observation magnification, the defect position on the image field is designated by, e.g., a cursor, and the designated position is moved to the observation field of the observation unit 15 to allow observation at a higher magnification. When image data including defects is read out, a mark (a cross pattern or an arrow) indicating the presence of a defect or a display in a color identifiable from other portions may be added at a defect position on the image display unit such as a TV monitor. At this time, it is preferable that the image fields including defects to be displayed be read out from the storage unit in the descending order of the defect sizes.

Note that various other image processing methods are available in addition to the above-mentioned image processing method. For example, as a simplest method, a method of performing defect inspection for a reticle (glass blank) without any pattern by dark field illumination is known. In this case, since only defects such as foreign matters shine by dark field illumination, only defects can be easily extracted by binarizing dark field images.

The fourth embodiment of the present invention will be described below. In this embodiment as well, the defect inspection apparatus shown in FIG. 12 is used. The defect inspection method of this embodiment is most efficient for shortening the time required for the inspection process. More specifically, in this embodiment, a determination criterion is set in advance before inspection. For example, the determination criterion is determined as follows. The upper limit of the number of detected defects is determined in units of ranks, and when, e.g., one defect of rank C or two or more defects of rank B are detected, the corresponding reticle is determined to be a defective product. Whether or not the determination criterion is satisfied is determined by the main control system 112 in FIG. 12.

Figure 17:
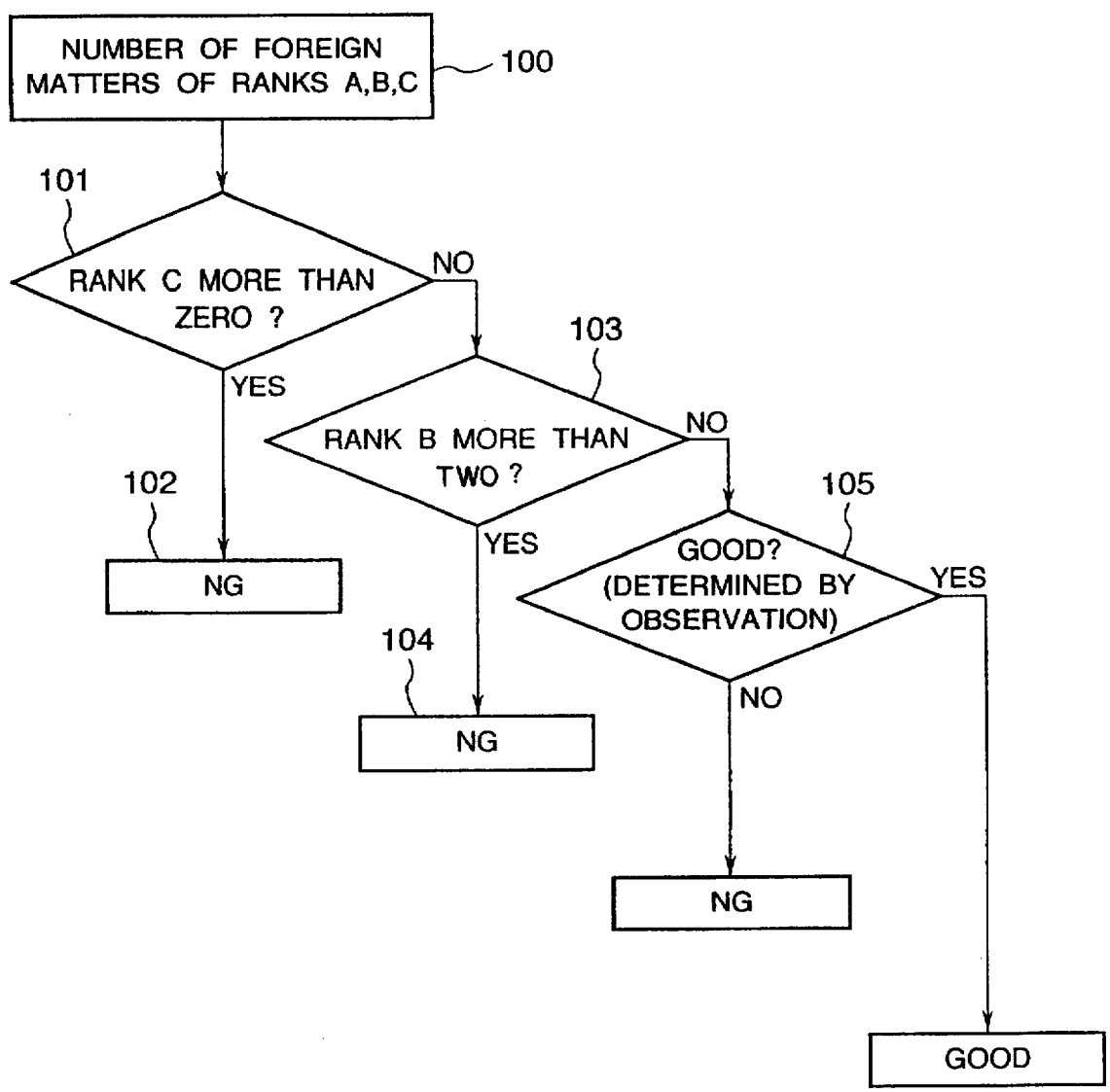
FIG. 17 is a flow chart showing a reticle determination process in the fourth embodiment of the present invention.

In other words, in this embodiment, the determination criterion is set in advance before inspection, and When it is clearly determined that a reticle is defective, the inspection process is terminated before observation. More specifically, the determination flow chart shown in FIG. 17 is used. After the end of inspection, data indicating the numbers of foreign matters of ranks A, B, and C are known (step 100). Since rank C represents a foreign matter having a large size, if at least one foreign matter of rank C is present (step 101), "NG" is determined. First determination means is arranged in the main control system 112, and if YES in step 101, "NG" is determined in step 102, and the corresponding reticle is handled as a defective reticle without performing microscope observation. However, if it is determined in step 101 that the number of foreign matters of rank C is zero, the flow advances to step 103, and reticles are sorted based on the number of foreign matters of rank B. This sorting operation is achieved by second determination means in the main control system 112. Rank B corresponds to a foreign matter of a middle size. If the number of foreign matter of rank B is small, such foreign matters may be ignored, but if it is too large, "NG" is determined (step 104). If the number of foreign matters of rank B is 2 or less, defects are observed one by one using the observation unit, and an operator determines whether or not the reticle is good (step 105). In this manner, the numbers of foreign matters are compared in units of sizes to sort reticles by automatic determination, thus omitting unnecessary observation of foreign matters.

In FIG. 12, when inspection of the reticle 1 is started by light beam scanning, and the light beam L2 is scanned in the X direction even slightly or the reticle 1 is fed in the Y direction even slightly, if the determination criterion is exceeded (is not satisfied), inspection by means of light beam scanning is interrupted at that time, and observation using the observation unit 15 is inhibited. However, in some cases, such defects may be required to be observed using the observation unit 15 like in analysis for the causes of defects for the future. In order to allow such analysis, it is preferable to allow selection of the above-mentioned automatic determination mode or a manual determination mode. More specifically, in the automatic determination mode, inspection is terminated when the determination criterion is exceeded; in the manual determination mode, inspection is terminated as in the automatic determination mode, or the reticle 1 is moved to the observation field of the observation unit 15 to allow observation of defects detected by the current inspection.

Note that the defect inspection apparatus of each of the above embodiments often comprises a case for storing reticles, and a feed unit for feeding a reticle from the reticle case to a foreign matter inspection unit. In particular, the reticle case is often designed to set a plurality of reticle cases. For example, five sets (five reticle cases) are assumed to be set.

At this time, when reticles are stored in all the five cases, and five reticles are continuously inspected, the above-mentioned automatic determination mode is selected. After inspection, of the five reticles, good reticles upon comparison with the determination criterion are labeled "good" (in data processing), defective reticles are labeled "defective", and all the reticles are returned to the reticle cases. After the end of continuous inspection of the five reticles, when an operator wants to observe foreign matters on the reticles labeled "defective" upon checking of inspection data (labels), the corresponding reticle may be directly fed to the foreign matter observation unit on the basis of the display shown in FIG. 16A, and foreign matter observation may be allowed by the above-mentioned method. Of course, since the operator may want to observe reticles labeled "good", it is preferable if selection between whether continuous processing is performed or reticles returned to the cases after inspection are fed again from the cases to allow foreign matter observation can be arbitrarily made. This control can also provide another practical merit. This is because a reticle is naturally free from any foreign matters if the number of attached foreign matters is zero, and no observation is required any way if the number of foreign matters is zero. If foreign matters are observed at the same time only when they are detected, an operator can perform observation at any time he or she wants. Therefore, the operation can be performed very effectively.

In each of the first to fourth embodiments above, the defect inspection apparatus for scanning the light beam relative to the reticle 1 has been described. In addition, the above-mentioned embodiments can be applied to a defect inspection apparatus which forms a slit-shaped irradiation region, parallel to the X direction, on a reticle by obliquely irradiating a slit beam onto the reticle, and scanning the light beam on the entire surface of the reticle by moving the slit-shaped irradiation region relative to the reticle in the Y direction.

In each of the above-mentioned embodiments, the object to be subjected to defect inspection is a reticle. However, the present invention can be similarly applied to a case wherein the object to be subjected to defect inspection is a wafer or a printed circuit board. In this manner, the present invention is not limited to the above-mentioned embodiments, and may adopt various arrangements without departing from the scope of the invention.

What is claimed is:

1. A defect display method comprising the steps of:
   irradiating inspection light onto a surface to be inspected of an object to be inspected;
   generating signals by photoelectrically converting scattered light from defects on the surface to be inspected; and
   assigning, based on magnitude of the generated signals, a defect signal to each of a plurality of imaginary cells obtained by dividing the surface to be inspected at predetermined pitches in a first direction and a second direction perpendicular to the first direction, and displaying, based on the assigned defect signals, an inspection result,
   wherein when defect signals are assigned to a plurality of neighboring cells due to a defect that occupies said neighboring cells, only a maximum defect signal of the defect signals assigned to said neighboring cells is displayed as the inspection result for said neighboring cells, thereby indicating the presence of the defect only in the cell having said maximum defect signal.

2. A method according to claim 1, wherein the maximum defect signal is obtained by removing smaller defect signals in N×M cells including N cells in the first direction and M cells in the second direction (N and M integers not less than 2).

3. A method according to claim 2, wherein N×M cells are scanned in the first and second directions and largest defect signals are obtained for successive groups of N×M cells by removing smaller defect signals, unit said maximum defect signal is left.

4. A method according to claim 2, wherein in the N×M cells are 2×2 cells.

5. A method according to claim 3, wherein the N×M cells are 2×2 cells.

6. A defect display method comprising the steps of:
   irradiating inspection light onto a surface to be inspected of an object to be inspected;
   generating signals by photoelectrically converting light from defects on the surface to be inspected;
   assigning, based on magnitude of the generated signals, a defect signal to each of a plurality of imaginary cells obtained by dividing the surface to be inspected at predetermined pitches in a first direction and a second direction perpendicular to the first direction;
   scanning 2×2 cells in the first and second directions so as to inspect successive groups of 2×2 cells;
   when a scanned group of cells has at least one defect signal exceeding a predetermined threshold, removing each such signal other than a maximum one in the scanned group, except in a case where such signal is for a cell disposed on a first diagonal of the scanned group, on which the cell having the maximum signal is also disposed, and where signals for cells disposed on a second diagonal of the scanned group do not exceed the predetermined threshold; and displaying an inspection result based on defect signals remaining after the scanning and removing steps.

7. A defect inspection method comprising the steps of:

irradiating inspection light onto a surface to be inspected of an object to be inspected;

detecting defects on the surface to be inspected based on signals obtained by photoelectrically converting scattered light of the inspection light from the surface to be inspected, and determining sizes of the detected defects;

observing at least one of the detected defects at a predetermined magnification in accordance with a descending order of defect size that is obtained based on the determination results; and terminating defect inspection of the object to be inspected when a defective portion is found as a result of the observation.

8. A defect inspection method comprising the steps of:

irradiating inspection light onto a surface to be inspected of an object to be inspected;

determining a size of a maximum defect in each of a plurality of imaginary cells, which are obtained by dividing the surface to be inspected and have a predetermined size, based on a signal obtained by photoelectrically converting scattered light of the inspection light from the surface to be inspected;

observing at least one of the cells including a defect among the plurality of cells at a predetermined magnification in accordance with a descending order of maximum defect size that is obtained based on the determination results; and terminating defect inspection of the object to be inspected when a defective portion is found as a result of the observation.

9. A defect inspection method comprising the steps of:

irradiating inspection light onto a surface to be inspected of an object to be inspected;

detecting at least one defect on the surface to be inspected based on a signal obtained by photoelectrically converting scattered light of the inspection light from the surface to be inspected, and determining a size of the detected defect; and terminating defect inspection of the object to be inspected when at least one of a case wherein the number of detected defects exceeds a predetermined allowable value and a case wherein there is a defect which has a determined defect size exceeding a predetermined allowable value occurs.

10. A defect inspection apparatus comprising:

a light scanning device which scans a surface to be inspected of an object to be inspected with inspection light;

a scanning position measurement device which measures scanning position of the inspection light on the surface to be inspected;

a light-receiving device which photoelectrically converts scattered light of the inspection light from the surface to be inspected;

a defect determination device which detects defects on the surface to be inspected based on an output signal from said light-receiving device, and determines sizes of the detected defects;

memory for storing sizes and positions, on the surface to be inspected, of defects, based on size determination results from said defect determination device and an output signal from said scanning position measurement device;

an observation device for observing the detected defects on the surface to be inspected at a predetermined magnification; and a controller which controls a positional relationship between the object to be inspected and the observation device based on sizes and positions, on the surface to be inspected, of the defects stored in said memory, so that the defects are observed in accordance with a descending order of size.

11. An apparatus according to claim 10, further comprising a display for displaying the sizes and positions of the defects stored in said memory.

12. A defect inspection apparatus comprising:

a light scanning device which scans a surface to be inspected of an object to be inspected with inspection light;

a scanning position measurement device which measures scanning position of the inspection light on the surface to be inspected;

a light-receiving device which photoelectrically converts scattered light of the inspection light from the surface to be inspected;

a defect determination device which detects defects on the surface to be inspected based on an output signal from said light-receiving device, and determines sizes of the detected defects;

memory for storing sizes of maximum defects in imaginary cells, which are obtained by dividing the surface to be inspected and have a predetermined size, and positions on the surface to be inspected of cells having defects, based on size determination results from said defect determination device and an output signal from said scanning position measurement device;

an observation device for observing the detected defects on the surface to be inspected at a predetermined magnification; and a controller which controls a positional relationship between the object to be inspected and said observation device based on the sizes of the maximum defects and the positions of the cells on the surface to be inspected stored in said memory, so that the cells having the defects are observed in accordance with a descending order of maximum defect size.

13. An apparatus according to claim 12, further comprising a display for displaying the sizes of the defects and the positions of the cells on the surface to be inspected, which are stored in said memory.

14. An apparatus according to claim 12, wherein an observation field of said observation device has a size which is larger than said predetermined size of said cells.

15. A defect inspection apparatus comprising:

a light scanning device which scans a surface to be inspected of an object to be inspected with inspection light;

a scanning position measurement device which measures scanning position of the inspection light on the surface to be inspected;

a light-receiving device which photoelectrically converts scattered light of th einspection light from the surface to be inspected;

a defect determination device which detects defects on the surface to be inspected based on an output signal from said light-receiving device, and determines sizes of the detected defects;

memory for storing sizes and positions, on the surfaces to be inspected, of defects, based on size determination results from said defect determination device and an output signal from said scanning position measurement device;

a comparison section which compares a number of detected defects per rank, in at least one of a plurality of ranks corresponding to different sizes of defects, with a predetermined allowable value; and a determination section which determines, based on a comparison result from said comparison section, whether or not the object to be inspected is defective.

16. An apparatus according to claim 15, wherein said comparison section compares the number of defects belonging to a rank, corresponding to a maximum defect size stored in said memory, with the predetermined allowable value.

* * * * *